(12) United States Patent
Saadat

(10) Patent No.: US 11,904,154 B2
(45) Date of Patent: Feb. 20, 2024

(54) ARTIFICIAL HEART SYSTEM

(71) Applicant: Mohammad Mohsen Saadat, Soest (DE)

(72) Inventor: Mohammad Mohsen Saadat, Soest (DE)

( * ) Notice: Subject to any disclaimer, the term of this patent is extended or adjusted under 35 U.S.C. 154(b) by 785 days.

(21) Appl. No.: 16/941,488

(22) Filed: Jul. 28, 2020

(65) Prior Publication Data

US 2020/0353141 A1 Nov. 12, 2020

Related U.S. Application Data

(63) Continuation-in-part of application No. PCT/EP2020/052058, filed on Jan. 28, 2020.

(30) Foreign Application Priority Data

Jan. 28, 2019 (DE) ...................... 10 2019 000 611.9

(51) Int. Cl.
| | |
|---|---|
| *A61M 1/10* | (2006.01) |
| *A61M 60/148* | (2021.01) |
| *A61M 60/258* | (2021.01) |
| *A61M 60/405* | (2021.01) |
| *A61M 60/892* | (2021.01) |
| *F16K 15/03* | (2006.01) |

(Continued)

(52) U.S. Cl.
CPC ........ *A61M 60/148* (2021.01); *A61M 60/196* (2021.01); *A61M 60/258* (2021.01); *A61M 60/268* (2021.01); *A61M 60/405* (2021.01); *A61M 60/427* (2021.01); *A61M 60/585* (2021.01); *A61M 60/837* (2021.01); *A61M 60/892* (2021.01); *A61M 60/894* (2021.01); *F16K 15/035* (2013.01); *F16K 15/144* (2013.01); *F16K 27/00* (2013.01); *A61M 2205/04* (2013.01); *A61M 2205/3337* (2013.01); *A61M 2210/125* (2013.01)

(58) Field of Classification Search
CPC ........ A61M 1/10; A61M 1/12; A61M 1/1086; A61M 1/122
See application file for complete search history.

(56) References Cited

U.S. PATENT DOCUMENTS

| | | |
|---|---|---|
| 3,148,696 A | 9/1964 | Hoke |
| RE27,399 E | 6/1972 | Urso |

(Continued)

FOREIGN PATENT DOCUMENTS

| | | |
|---|---|---|
| DE | 2949469 B1 | 5/1981 |
| DE | 3316101 C1 | 8/1984 |

(Continued)

OTHER PUBLICATIONS

Gremium setzt enge Grenzen für neue Herz-OP. In: Spiegel online, Jan. 23, 2015, 1-3, English translation attached.

*Primary Examiner* — Matthew W Schall
(74) *Attorney, Agent, or Firm* — BROWDY AND NEIMARK, P.L.L.C.

(57) ABSTRACT

An artificial heart system for human beings or other creatures, comprises at least one half of the heart, to be implemented into the body, instead of or in parallel to the biologic heart or outside of human body for example for a portable dialysis apparatus, maintaining or supporting at least one blood circulatory system or circuit of the human being or the other creature as a pump, completely or partially, and at least one drive unit and at least one control unit, preferably to be placed outside the body.

28 Claims, 35 Drawing Sheets

(51) Int. Cl.
  *F16K 15/14*    (2006.01)
  *F16K 27/00*    (2006.01)
  *A61M 60/427*   (2021.01)
  *A61M 60/268*   (2021.01)
  *A61M 60/196*   (2021.01)
  *A61M 60/894*   (2021.01)
  *A61M 60/585*   (2021.01)
  *A61M 60/837*   (2021.01)

(56) References Cited

U.S. PATENT DOCUMENTS

| | | |
|---|---|---|
| 3,938,197 A | 2/1976 | Milo |
| 4,222,127 A | 9/1980 | Donachy et al. |
| 4,308,885 A | 1/1982 | Geisseler |
| 4,351,358 A | 9/1982 | Ogle, Jr. |
| 4,397,049 A | 8/1983 | Robinson et al. |
| 4,463,248 A | 7/1984 | Katzman et al. |
| 4,465,102 A | 8/1984 | Rupp |
| 4,611,578 A | 9/1986 | Heimes |
| 4,648,385 A | 3/1987 | Oumi et al. |
| 4,731,076 A | 3/1988 | Noon et al. |
| 4,771,925 A | 9/1988 | Stoeffler |
| 4,863,461 A | 9/1989 | Jarvik |
| 5,263,895 A | 11/1993 | Kraus et al. |
| 5,458,468 A | 10/1995 | Ye et al. |
| 5,503,186 A | 4/1996 | Orejola |
| 5,628,792 A | 5/1997 | Lentell |
| 5,775,357 A | 7/1998 | Regna et al. |
| 6,035,896 A | 3/2000 | Liardet |
| 8,141,587 B2 | 3/2012 | Doig |
| 10,344,882 B2 | 7/2019 | Skorupa |
| 10,487,740 B2 | 11/2019 | Dehais |
| 10,487,955 B2 | 11/2019 | Czarnecki |
| 10,670,158 B2 | 6/2020 | Wilhelm et al. |
| 10,935,148 B2 | 3/2021 | Kielczykowski et al. |
| 10,948,093 B2 | 3/2021 | Czarnecki et al. |
| 2006/0016479 A1 | 1/2006 | Gonzales |
| 2007/0131285 A1 | 6/2007 | Zika-Beyerlein et al. |
| 2015/0308681 A1 | 10/2015 | Martin |
| 2017/0167618 A1 | 6/2017 | Czarnecki |
| 2018/0087680 A1 | 3/2018 | Wilhelm et al. |
| 2020/0353141 A1 | 11/2020 | Saadat |

FOREIGN PATENT DOCUMENTS

| | | |
|---|---|---|
| DE | 689 06 403 T2 | 6/1993 |
| DE | 698 20 603 T2 | 1/2004 |
| DE | 69627510 T2 | 1/2004 |
| DE | 102019000611 A1 | 7/2020 |
| GB | 190926783 A | 9/1910 |
| JP | H025966 A | 5/1983 |
| JP | S6389469 U | 6/1988 |
| JP | 2006346440 A | 12/2006 |
| WO | 2020157054 A1 | 8/2020 |

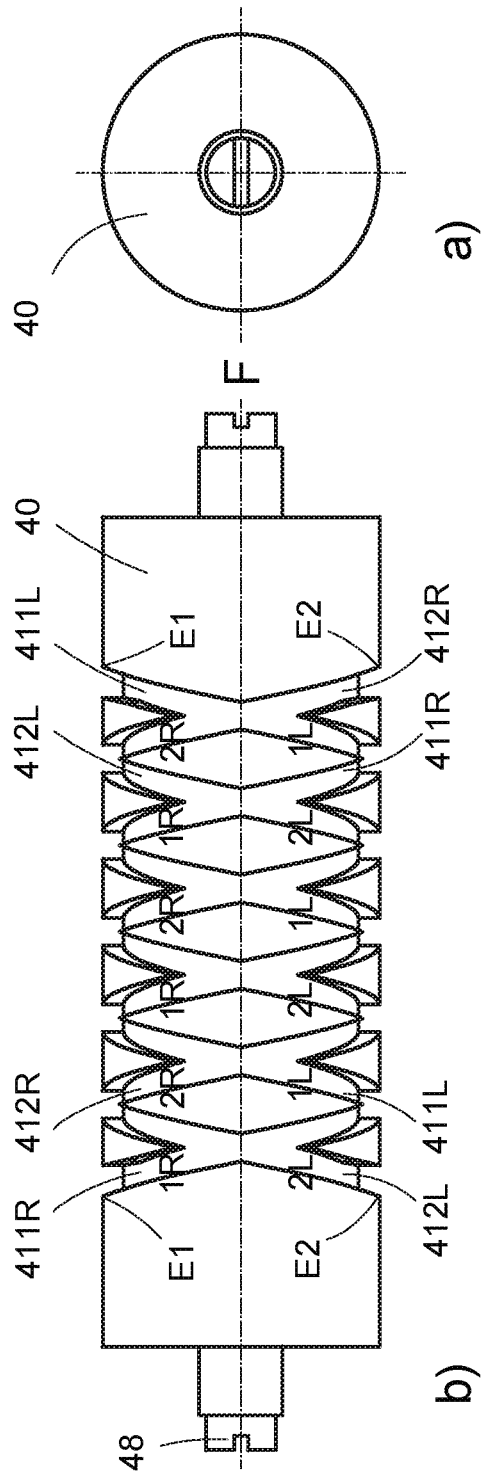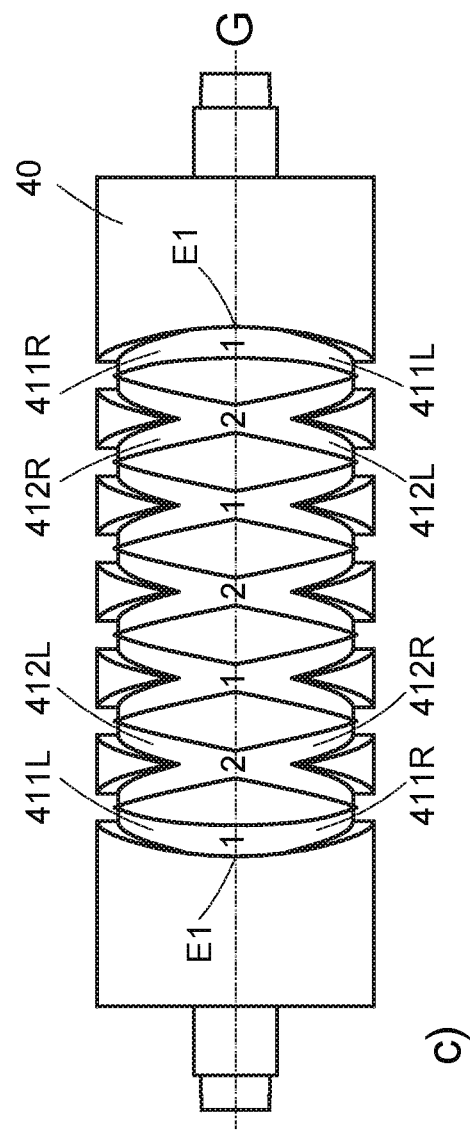
Fig. 13

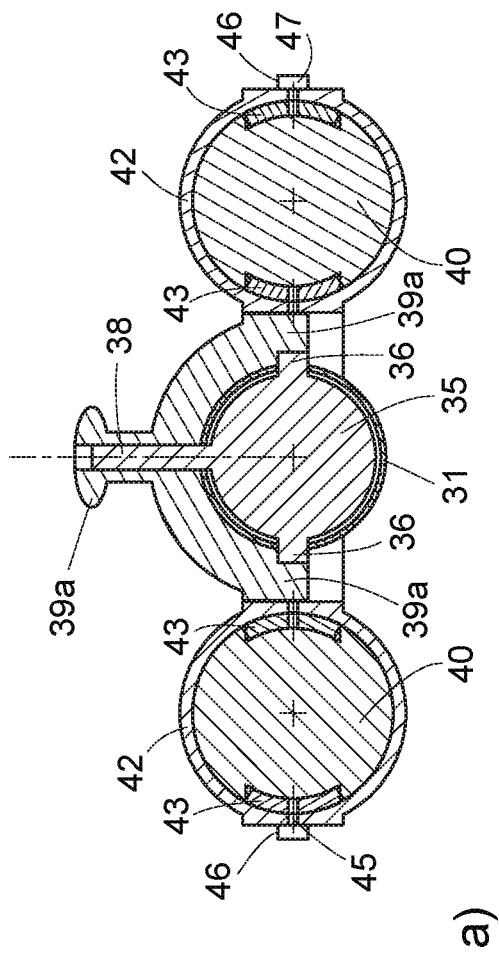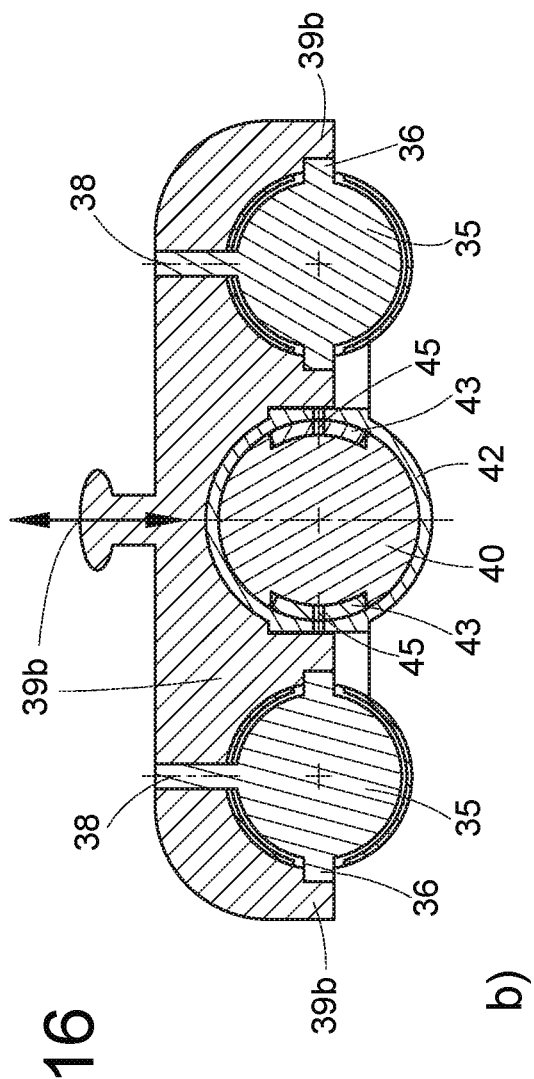
Fig. 16 ial Heart System

ARTIFICIAL HEART SYSTEM

This application is a continuation-in-part of International Patent Application No. PCT/EP2020/052058 filed Jan. 28, 2020, which designated the U.S. and claims the benefit of priority to German Patent Application No. DE10 2019 000 611.9 filed Jan. 28, 2019, each of which is hereby incorporated in its entirety including all tables, figures and claims.

The invention described in this document represents an artificial heart system for human beings or other creatures, comprising at least one half of the heart, to be implemented into the body, instead of or in parallel to the biologic heart or outside of human body for example for a portable dialysis apparatus, maintaining or supporting at least one blood circulatory system or circuit of the human being or the other creature as a pump, completely or partially, and at least one drive unit and at least one control unit, preferably to be placed outside the body.

BACKGROUND OF THE INVENTION

Numerous artificial hearts exist, to be inserted into the body and to be actuated electrically or from outside by means of compressed air. Due to the high energy demand of a heart, it is not possible to find an energy source to be implemented permanently inside the body; therefore it must be placed outside the body, exchangeable and rechargeable.

Available pumps, devices and units replacing or supporting the heart usually dispose of a considerable size, are not easy to handle and first of all generate noise. Furthermore, these artificial hearts are based on technical pumps giving rise to mechanical damage of the blood cells over time, or they make use of elastic membranes, which after a while become porous, leaky and are finally torn.

DE 689 06 403 T2 shows an artificial heart composed of two halves. Each half of the heart features three chambers. Between these chambers, two elastic membranes (10 and 11) are contained. During each heart contraction, the drive pump (22) presses a liquid against the membrane (11), which for its part transmits the pressure to the liquid between the two membranes (10 and 11) and from there to membrane (10) of the blood chamber (9a). During this procedure, on the one hand liquid from the intermediate space between the two elastic membranes (10 and 11) returns to the storage tank (13), on the other hand from the blood chamber (9a) it penetrates into the artery (7). During aspiration of the drive fluid by the pump (22), the blood flows from vein opening (3) into blood chamber (9a). Simultaneously the liquid from the storage tank (13) returns to the space between the two membranes (10 and 11). The partitioning of the two liquids depends on the flow resistance of each liquid and differs with respect to the halves of the heart. As described, the required cardiac output cannot be ensured. The invention entails some serious drawbacks and problems which up to now could not be corrected. For example two motors and two pumps are located within the body despite the risk of heat and fire. Furthermore it is not possible to discharge the blood chamber (9a) completely, which causes the risk of thrombosis. The synchronous run of the motors is not ensured; and the function of the heart valves has not been described.

Furthermore the blood within the artificial heart comes into contact with several different materials. Due to the continuously repeated inversion of the sense of rotation of the two electric motors, their lifetime is considerably reduced.

DE 698 20 603 T2 shows an artificial heart with drives and pumps located directly inside the heart as well, with all the drawbacks mentioned above, and inaccessible inside the body.

SUMMARY OF THE INVENTION

The purpose of the invention consists in the task of developing an artificial heart with at least partial improvement with respect to these drawbacks. It is particularly intended to make available a powerful but simple heart, working silently and ensuring a high safety standard, preferably to permanently maintain or to support at least one of the two circulatory systems, to be implemented in the body or to be installed outside the body of human beings or other creatures, and to be operated by a drive and control unit placed outside the body, in a configuration enabling in an emergency case first help measures to be carried out by the patient himself, wherever he may be.

The invention implements this task by means of the features that characterized by these independent claims.

Dependent-claims represent beneficial further developments of the invention.

The artificial heart representing the core of this invention is intended for maintaining and/or supporting at least one circulatory system of human beings and/or other creatures. It comprises at least one and particularly two hermetically sealed halves of a heart with one blood chamber and one drive chamber each. Furthermore, each half of the heart features a divisible hard shell. The blood chamber is made available by a bag, with this blood bag being placed in immobilized state against the wall of the hard shell at least in sections and particularly up to the half. The second half of the blood bag is shifted into the first half, by means of pressure originating from the drive chamber, without stress and preferably without kinking in a circumferentially unrolling bending procedure, at least in sections and preferably completely. Furthermore the drive bag is placed in immobilized state against the wall of the hard shell at least in sections and particularly up to the half, with the second half back to back to the blood bag, and generates preferably without stress and without strain or kinking the unrolling procedure of the bending wave.

Preferably at the back of the movable half of the blood and drive bags, teeth in a shape similar to parallels of latitude are provided, like bulges by material accumulation and/or by insertion or incorporation of stiff rings, particularly mutually connected like chain links.

It is particularly preferred to place at least one elastic pad between the two bags, particularly at least one lenticular convex-shaped elastic pad.

The bags are preferably woven from biologic thread, at least in sections.

In convenient designs, each hard shell comprises two half-shells, to be inserted into each other by a positive and negative interlocking detachable connection with a conical interface.

Beneficial designs feature longitudinal and transversal grooves on the inner surface of the half of the heart respectively of the shell, particularly used as third chamber for accommodation of a viscous lubricating and sealing agent.

Furthermore, for the inner surface of the half of the heart respectively of the shell, longitudinal and transversal grooves with a connection to the outside are recommended, acting as third chamber for regulation of cardiac output.

It is particularly preferred that positive and negative elements are provided at the half of the heart, so that a second half of the heart can be rotated with respect to its longitudinal axis by 180°, then attached to the first half, so that in common they maintain as blood pump both circulatory systems of a human being or another creature.

It is preferred that at least on drive medium represents a liquid.

In useful further developments, the drive fluid is pumped into (and out from) the drive bag by means of a cylinder-piston unit, with the piston rod actuated by a spindle drive comprising a spindle featuring a double-start right-left infinite loop.

It is preferred to pump the drive fluid into and out from the drive bags in alternating mode, by means of a cylinder-double-piston unit, with the piston rod actuated by one or two spindle drives comprising a spindle featuring a double-start right-left infinite loop.

In other designs, the driving fluid is pumped into and out from the right and left drive bags by two cylinder-piston units simultaneously, with the piston rods actuated by one or two spindle drives comprising a spindle featuring a double-start helical groove running at the right and at the left in an infinite loop.

It is particularly preferred that at least one inlet and one outlet valve of the blood chamber is provided, composed of or featuring triangular-shaped or triangular hard lamellae, grouped in circular configuration around a polygonal, preferably hexagonal, through hole of a valve ring and swiveling by pivot.

Preferably at two sides of the valve lamellae, lateral lamellae by means of pivots are configured and grouped, so that they are folded up radially towards outside behind the valve lamellae when the valve is closed, meanwhile sealing completely the gap between the valve lamellae and thus their increasing bending resistance.

It may also be useful to insert—instead of the lateral lamellae—elastic elements like shackles between the valve lamellae.

In other further developments, at least one grid structure is installed to the valve ring, open respectively open to flow, preferably of pyramidal shape, used as support and improved seal for the valve lamellae. The opening of the valve lamellae is limited by leaning the bulge-shaped webs against the tube piece.

It is recommended to monitor the valve by means of a miniature camera or an optical sensor.

It is preferred that a pressure sensor is intended to be installed, particularly within the hard shell, measuring the current blood pressure and transmitting the result to a control unit.

It is convenient to make use of a mechanical coupling to separate the connection between drive systems and piston rods (preferably manually) in case of need, to be able to manually operate the cylinder (double) piston units and after successful troubleshooting to reestablish the connection with the push of a button, or other means to reengage the coupling.

The outer surface of the connections of the halves of the heart is preferably equipped with positive curvatures, and the artery, vein or the connection hose are attached in a preferably loose and non-slip configuration, by means of at least one quick-release fastener preferably with barbs and/or negatively curved surface and particularly at least one securing element.

The heart basic to this invention comprises at least one and preferably two halves of the heart. Each half of the heart is hollow and features a hard shell hermetically sealed with respect to air and liquids, and composed of at least two parts.

Each half of the heart features at least two chambers, one blood and one drive chamber. The blood chamber preferably consists completely of a blood bag, maintaining the bloodstream of one of the two blood circulatory systems, through the lung or through the rest of the body, on the basis of its rhythmic pulsation, by means of the drive chamber.

In filled state the blood bag essentially fills the entire volume, particularly the entire volume of one half of the heart. The drive chamber as well consists as well preferably completely of a drive bag with its volume in filled state essentially and particularly completely corresponding to the volume of one half of the heart, and is placed in opposite position to the blood bag.

The hard shell of each half of the heart preferably features a three-dimensional elliptical shape, and is equipped at least at one of its outer longitudinal surfaces with fasteners in form of plug-in connectors, enabling to group two identical or equal halves of a heart on a vertical axis in parallel to the sternum, mutually mirrored by 180°, and to insert them into each other by interlocking connection. The plug-in connectors of the two halves of the heart feature film joints in parallel to their vertical mirror axis, allowing an elastic angle change of both halves of the heart with respect to each other.

An entire heart is preferably composed by inserting into each other positively and negatively profiled fasteners, or by mutually screwing of two identical or equal halves of the heart, with each of the halves featuring its own closed hard shell, one blood chamber and one drive chamber located within.

An artificial heart designed this way disposes of size and geometrical shape of a natural heart, preferably however flatter. One half of a heart preferably disposes of the geometrical shape of an ellipsoid, looking like an egg in oval manner compressed at its equator.

The thickness of the wall of the hard shell of each half of the heart preferably amounts to some tenths of a millimeter. It is composed of at least two parts, preferably two half shells, with a separating line running longitudinally through the poles, slanted diagonally, or as illustrated below, transversally along the equator. The separating line between the two half shells at the equator, or somewhat inclined to it, forms an ellipse up to a circle, with an inserted plane approximately vertically to the main axis of the hard shell, or somewhat inclined to it. The two half shells together with their comprised blood and drive chambers are inserted into each other, tight with respect to air and liquid, or mutually screwed or clamped. For the two half shells, a step has to be provided preferably at the separating edges at the inner surface, so that both steps after assembly of the two half shells, in their interior along their common separating gap, form a closed and elliptical circumferential groove.

This circumferential groove and other longitudinal and transversal grooves on the inner surface of the two half shells, running like longitudes and latitudes on a globe, together form a third chamber, the lubricating chamber through which a lubricating agent like paraffin runs all around between the two chambers (blood and drive chamber) and the inner wall of the hard shell.

The half shells are preferably manufactured by injection molding of biologically compatible plastics and/or they are produced by three-dimensional printing or plotting of plastics or a plastic/metal mixture. In case of need, a surface layer composed of precious metal like gold, platinum, titanium or a ceramic coat may be applied. Items produced on the basis of aluminum alloys may be electrochemically anodized.

The interior of each half of a heart features at least two, preferably three chambers independent of each other, one blood chamber for the blood, one pressure and suction chamber acting as drive chamber, and optionally a third chamber as intermediate space between the other two mentioned chambers, for a lubricating agent, with its volume at the same time determining the cardiac output. All the chambers are preferably positioned inside the hard shell beside each other, tight with respect to air and liquid, or on top on each other or diagonally with respect to each other. The chambers of each half of the heart may also be grouped coaxially into each other. At least the blood chamber must consist of a very thin material, biologically compatible, guaranteeing tensile strength, very flexible, supple, pliant and deformable without resistance, like the threads of silkworms or spiders, or of a very thin synthetic thread like Nylon, PET or Perlon in the form of a balloon, a pad like a bag with two cylindrical sleeves woven in one piece or of PUC produced by 3D printing.

The blood and drive bags rather pads are wetted preferably from outside with a viscous liquid as lubricating agent, like paraffin, preferably from a third chamber. They are positioned preferably to one half each, at the wall of their half shell which features their connection. The other second halves are preferably placed back to back with the lubricating agent in the intermediate space, migrating back and forth together, rhythmically pulsating, from the connector of the drive medium to the blood connections respectively to the aorta valve. During this cycle they change their volume preferably from a value close to zero up to 98% of the volume of the hard shell, depending on the variable volume of the lubricating agent, without being stretched, kinked or folded during this operation and deformation. The deformation of the blood bag is caused particularly by a circumferential bending wave, respectively deformation wave, migrating up and down over the second half, starting from a position at ca. two thirds of the lower half shell up to the equator of the half of the heart. One of ordinary skill in the art would understand that the terms "upper half shell" and "lower half shell" refers to the orientation of the half shells in a vertical human body (standing) that is often depicted in anatomy books. These shell halves can also be referred to as the "first half of shell" and the "second half of shell".

The viscous liquid within the third chamber preferably as a sliding layer reduces the friction between the two chambers and the internal wall of the hard shell, maintains the supple and dense structure of the tissue of the bags, and additionally enables the load and the pressure to be distributed uniformly on the two bags. The quantity respectively the volume of the viscous liquid between the two chambers is used for regulation of the cardiac output per beat. For regulation of the quantity of this sliding liquid and its exchange, the third chamber features a connector at the hard shell, preferably in proximity to the equator. Starting from this connector, a thin hose is guided in parallel to the drive hose from the inside of the body towards outside to the pump unit and control unit, at a corset placed on the chest, on a belt or another position of the body.

The blood chamber is composed of a preferably elliptical bag preferably woven in one piece, with a cylindrical inlet and cylindrical outlet, like two sleeves from a bag. The blood bag is preferably placed directly within the circulatory system, either in the right half of the heart in the low-oxygen circulatory system, pumping the blood flowing from the muscles and organs of the body towards the lung, or in the left half of the heart in the oxygen-rich circulatory system, pumping the blood coming from the lung towards the muscles and organs of the body. The blood bag is located particularly within the upper half shell, disposing of one opening each for inlet and outlet of the blood, which feature one check valve each, besides an optical system with integrated camera for remote diagnosis of the valve, and at least one pressure sensor within the immobile half for measurement of the blood pressure.

Both connectors of the blood chamber for the artificial heart—analog to the natural heart—are located in the upper zone of the hard shell, oriented towards the head. The center plane between the right and the left half of the heart, the ventricular septum (septum interventriculare cordis) is oriented approximately perpendicularly to the breast level, inclined by ca. 5 to 15° counterclockwise with respect to a straight spine. For both halves of the heart, openings for inlet and outlet of the blood are approximately symmetrical with respect to the mentioned center plane, with the two outlet openings, the pulmonary artery and the aorta, positioned close to the center plane of the heart, and the two inlet openings, the cava veins and the pulmonary veins, at a somewhat larger distance. This way the entire artificial heart may be composed of two identical halves, rotated by 180° with respect to the central longitudinal axis each. This configuration enables only one half to be exchanged in case of need or to be inserted in parallel to the natural heart as a support. The connectors of the blood bags are directly connected to the veins, so that the blood does not come into contact with any other material apart from the blood bag.

Preferably below or beside each blood chamber, the drive chamber is located. It is used to discharge the blood chamber by generating pressure, and to fill it again by generating suction within the hard shell of the half of the heart. The drive chamber is preferably composed of a bag as well, consisting of a tensile strength material, very flexible, supple and deformable without resistance, preferably woven in one piece, with a cylindrical connection. The connector is preferably located close to the apex cordis and is used for inlet and outlet of a drive fluid, which is preferably a component of the blood, e.g. saline or another fluid compatible to blood, e.g. coconut milk. As described for the blood bag, one half of the drive bag—here the lower half—is always placed against the wall of the lower half shell, whereas the upper half contacts the lower half of the blood bag, back to back, moving up and down with it in common.

For an extremely safe and durable version of the half of the heart according to this application, it is intended to weave the tensile strength threads of the two bags (blood and drive bag) in circumferential and longitudinal direction, similar to longitudes and latitudes. For each bag, the half with the connector is oriented towards outside in its half shell at the wall, wrinkle-free, whereas the other halves (the free halves) are mutually connected back to back, in the intermediate space, holding in place an elliptic pad filled with a gel or viscous paraffin or with medicinal silicone.

The bag with paraffin or silicone on the one hand ensures a homogenous and symmetrical upward and downward movement of the two halves of the bags, on the other hand prevents entry of the soft bags at the end of the half shells into inlet and outlet channels of the blood and the drive fluid. The pad filled with gel during rhythmic upward and downward movement of the two loose halves of the bag is held like a piston without rod in the inner space of the half of the heart, held in place by longitudinal threads and centered by means of transversal and circumferential threads.

During assembly of the half of the heart, preferably first the cylindrical connectors, the sleeves of the two bags are inserted into the corresponding connectors of the hard half shells, until the sleeves of each bag protrude from the connectors of the hard shell. After completion of this step, the lower half shell is equipped with its seal, and the two half shells are inserted into each other. Then the two bags in turn are pressurized by a gaseous medium, so that both halves of the bag are pushed against the interior walls of the hard half shell. The three connectors (sleeves) of the two bags are pulled back over their round connectors at the hard shell. Afterwards the two check valves are inserted through the sleeves into the connectors of the blood chamber.

From now on the connectors are ready for establishment of the connection of the two blood veins in the upper zone and a hose in the lower drive zone.

When a vein, an artery or an aorta has been pulled over the corresponding connector, the connection must be secured against unintended separation preferably by means of at least one quick-release made of plastics, similar to a cable strap. This way a safe and smooth transfer of the bloodstream between veins and blood chamber is ensured. It is also possible to sew the connectors of the blood bags, the sleeves, directly to the corresponding vein or artery.

The lower half shell contains the drive chamber with its connector, as well as the connector for viscous lubricant. It is possible to measure the pressure of the viscous lubricant outside the body. This represents an indicator for the blood pressure within the blood chamber as well.

The wall of the common contact area between both chambers (blood and drive chamber) is preferably designed in three dimensions in a manner preventing turbulent flow inside the blood chamber. For that purpose, reinforcing webs and struts have to be attached to the outer surfaces of the two bags, locally to be placed partially into present grooves and indentations at the inner wall of the hard shell. Their resistance determines the deformation and sequence of movements of the two cooperating chambers in the course of their work. The partially different wall thicknesses of blood and drive chamber in circumferential and longitudinal direction, enables the elasticity and the bending resistance of the wall of the bag to be determined in a targeted manner to optimize the sequence of the deformation during upward and downward movement, ensuring a permanently laminar flow of the blood into and out from the blood chamber, and a complete discharge of the blood chamber, without formation of wrinkles, by means of the lenticular bulge described above.

It is preferred to form within the flexible material, tissue or plastics like Polycarbonaturethan, called PCU, ring-shaped bulges on the rear face of the movable halves of the blood and drive bags placed over each other, like the teeth of a three-dimensional gear toothing with teeth and tooth gaps, similar to the parallels of latitudes on a globe, so that the teeth of one bag, while unrolling the two rear faces on each other, are inserted into the gaps of the other bag, and vice versa. The bags formed this way are called tooth bags. In basic configuration, the shape of the teeth is round, like a lantern gear toothing. In cross-section respectively normal section, the shape of an involute or cycloid is also possible.

The connector of the drive chamber of each half of the heart is coupled to a pump, preferably located outside the body, by means of an elastic hose.

An artificial heart working this way can also be placed outside the body. In this case, the connectors of the blood chamber are guided into the body by means of extension lines, and there connected to the veins and the arteries of the old and defective heart.

The pump of the drive fluid is preferably composed of two cylinder-piston units synchronized to each other, connected in series or in parallel. They are placed outside the body on the chest in a closed and waterproof case at a corset, or on a belt. The pump cylinder is attached preferably in horizontal orientation to the body of the human being or the creature, with the piston moving back and forth along the cylinder axis, pumping the drive fluid (saline or coconut milk) from the pump cylinder to the drive chamber, and vice versa. For each half of the heart, one cylinder-piston unit is provided; for the complete artificial heart two units are required, to be grouped in parallel beside each other, or in series on a common axis in tandem configuration or coaxially, inside or around each other. The configuration of the cylinder-piston units determines, whether the two halves of the heart supply blood to the arteries in turn, or (like a natural heart) simultaneously.

The piston rods of the pumps are moved back and forth preferably by one single electric motor, or by up to four electric motors in different mode, in redundant configuration. Besides the known pump principles like axial and radial piston pumps, internal and external gear pumps, the piston rods of the hydraulic cylinder-piston units are moved back and forth by means of a rotating disc and one or two eccentric stroke.

A particularly safe back and forth movement of the piston rods can be achieved in useful designs featuring one or two infinite loop spindle drives. In these configurations, one or two electric motors drive a spindle shaft with a preferably double-start infinite thread groove with two right-handed and two left-handed threads at constant angular speed; the rotation takes place always in one direction. The spindle drives are composed of a preferably hollow spindle drum (roll) with two mutually crossing thread grooves with right-handed and left-handed thread at its perimeter, single- or preferably double-start, so that the ends of the grooves tangentially merge into each other. This ensures a smooth, jerk and shock free automatic transition of the spindle nut from the end of a right-handed groove to a left handed groove, inverting its travel direction, with continuous rotation of the spindle drum always in one direction, the speed meanwhile being unchanged.

The spindle nut consists of a hollow cylinder without thread, like a tube piece, sliding over the spindle drum with minimum play. Within the spindle nut, at least one sliding block is provided in form of a three-dimensionally bent and rounded shuttle, radially coupled by a pin to the inner wall of the hollow cylinder, rotatable around the pin axis in both directions by ca. ±30°. Each spindle nut features the number of sliding blocks respectively shuttles corresponding to the number of parallel thread passages available on the spindle drum. For a spindle drum with two thread passages for instance, the spindle nut features two sliding blocks respectively shuttles, opposite to each other in mirrored configuration with respect to the rotary axis of the drum. They transmit the rotary motion of the spindle drum to a translational back and forth movement of the spindle nut, if the own rotation of the spindle nut is prevented. The outside of the spindle nut is connected to the piston rod of one pump with one piston rod or to the piston rods of two pumps, each with their own piston rod. For this reason, the spindle nut cannot rotate around its own axis. The mechanical connection of the piston rod to the spindle nut takes place by a manually actuated coupling. This connection in an emergency case, e.g. during failure of the electric drives, can be separated simply by pulling a button, thus disengaging the coupling. Afterwards piston rods and thus the pumps can be actuated manually.

In the case of two or more drive motors and spindle drives, it is recommended to mutually couple the spindle drums e.g. by gears.

The natural heart valves preferably are replaced by innovative artificial valves, to be inserted into the connectors of the openings for inlet and outlet of the blood, into the sleeves of the blood bags. The valves represent particularly separately manufactured and exchangeable modules, not only used in artificial hearts. These innovative items can be produced by pouring of plastics, injection molding or 3D printing. They are used as check valves working without external energy supply in numerous industrial branches, in medical technology as replacement for heart or venous valves, and in the building sector as check valves preventing backflow of water or sewage into channels or domestic lines.

They comprise several, at least three, but preferably six triangular-shaped and particularly equilateral lamellae, to be attached by their third side by means of joints, preferably film joints to the edges of a polygonal, preferably hexagonal through hole and particularly of such a bore, of a valve ring. Each blood chamber features two valves. The valve rings are housed in a step of the openings each, at the upper half shell, perpendicularly to the bloodstream.

The step is located within the blood inlet opening at its end, i.e. at a larger distance to the blood chamber, and within the blood outlet opening at its starting point. In order to enable the valve lamellae tightly to close during backflow of the blood, the two faces of isosceles of the lamellae are connected in a rotatable manner to another triangular-shaped lateral lamella each. The acute angle of this lateral lamella is located at a corner of a polygonal or hexagonal through hole or bore of the valve ring.

In closed state, the valve lamellae form a three- or multi-faced, e.g. a six-faced pyramid, and in opened state a half-pyramid up to a multi-faced (here in this example a twelve-faced) cylinder. In closed state of the valve, the faces of the lateral lamellae opposite to the acute angle, form a star with three up to several (here in this example: six) radial double blades. In order to enable the valve lamellae quickly and safely to close during back-flow of the blood, segment-shaped springing elements are provided between the back of the valve lamellae and the valve ring, permanently exerting a closing force on the valve lamellae.

Another version of the valve manages without the lateral lamellae; in this configuration the segment-shaped springing elements are attached preferably to two adjacent valve lamellae each.

An interesting beneficial version of the valve is characterized by a honeycomb-shaped open pyramid used as ring of the valve. In closed state, the valve lamellae are put on triangular-shaped openings at the faces of the pyramid of the valve ring. Towards outside, the opening of the valve lamellae is restricted by material projection (put on the tube of the valve) on the rear side of the valve lamellae.

All of these three valve versions are able to open and to close only actuated by blood flow, without supply of external energy.

A heart or half of a heart based on this design has preferably to be pre-assembled in clean-rooms under corresponding hygienic conditions. The drive chambers as well as the pumps are filled with drive fluid and vented. The connectors of the lubricating and regulating medium are connected to a storage tank as well, filled and vented. Then the artificial heart can be installed inside the body of a human being or of another creature, replacing the natural heart. First the cava veins have to be connected to the blood inlet openings of the right half of the heart, then the blood outlet opening of the right half of the heart to the pulmonary arteries. Afterwards the pulmonary veins are connected to the blood entry opening of the left half of the heart, then the aorta to the blood outlet opening of the left half of the heart. Later venting of the heart chambers is no more necessary, if this sequence is correctly followed.

The current value of the blood pressure is preferably supplied by a pressure sensor within the range of the blood chamber. The pressure of the lubricating and regulating medium can be measured at its connector or within a tank outside the body. It delivers the direct value of the systolic blood pressure or an indicator for that value. Valuable information on the state of the valves of the artificial heart can also be provided by small cameras in front of the valve modules, with light transmission through fiber optic cables.

All modules located outside the body are preferably accommodated in common together with a miniature computer in a waterproof case. To the sensors transmitting information on current blood pressure, heart rate, state of the valves and cardiac output to the computer, sensors are added transmitting oxygen content and breathing rate. On the basis of this information, the computer calculates the required blood flow rate and pulse rate to adjust them.

BRIEF DESCRIPTION OF THE DRAWINGS

The following illustrations show schematic:

FIG. 13 the spindle of the spindle drive with two-start groove spiral, running at the left and the right side in an infinite loop, and a connecting coupling at both sides to the single- or double-sided drive of the spindle.

a) shows the valve with six valve lamellae in a perspective view in closed position, b) the section through the center of two valve lamellae mutually opposed, c) the valve with six closed valve lamellae without case (51), d) a top view of the honeycomb shaped grid structure of the valve without valve lamellae FIG. 16 below a) a section through the mechanical coupling (39*a*) according to FIG. 11, perpendicularly to the piston rod and below b) a section through the mechanical coupling (39*b*) perpendicularly to the piston rods according to FIG. 14) as well.

Figure 17:
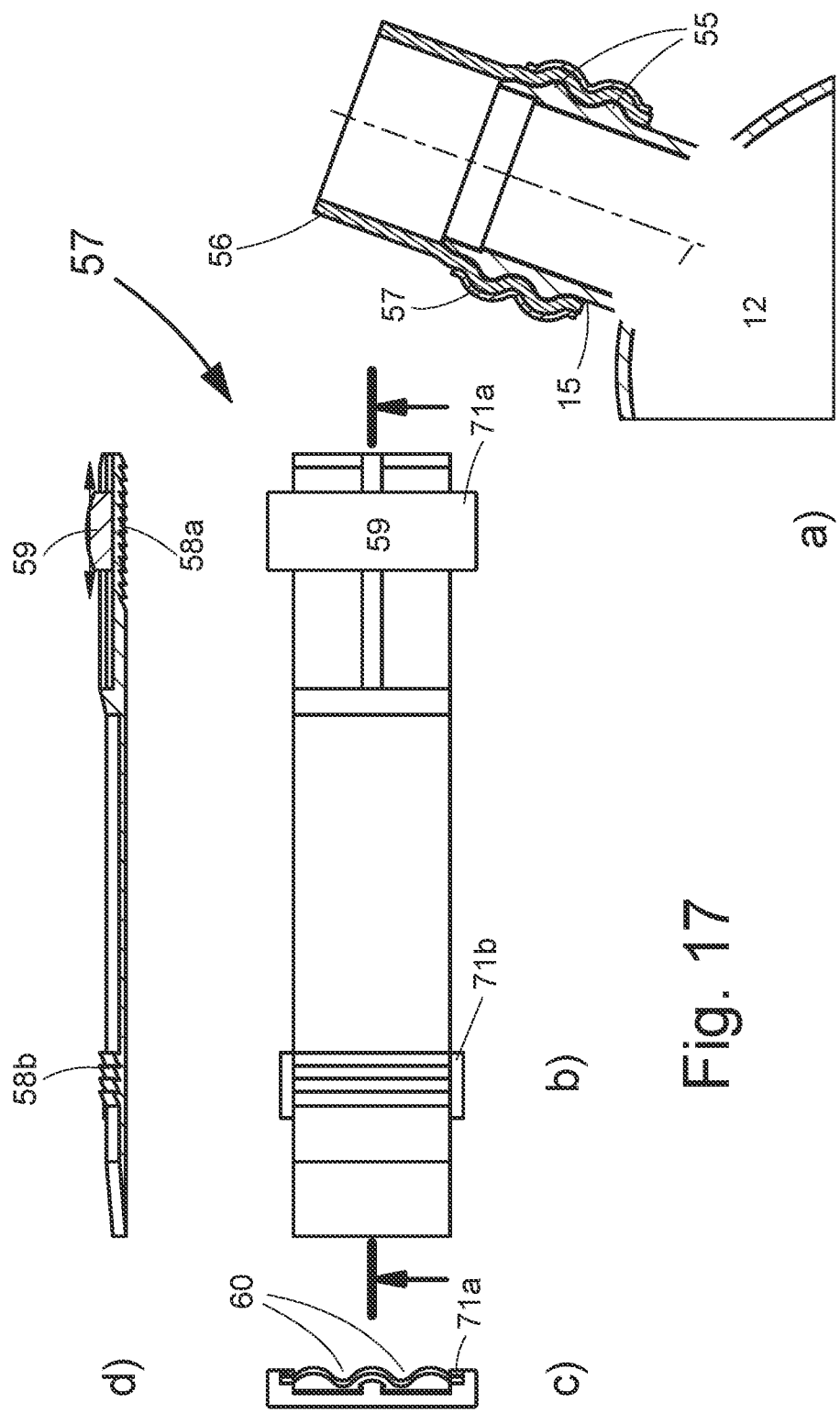

FIG. 17 a quick connector of veins and arteries to the connectors of the half shells of the heart.

Figure 18:
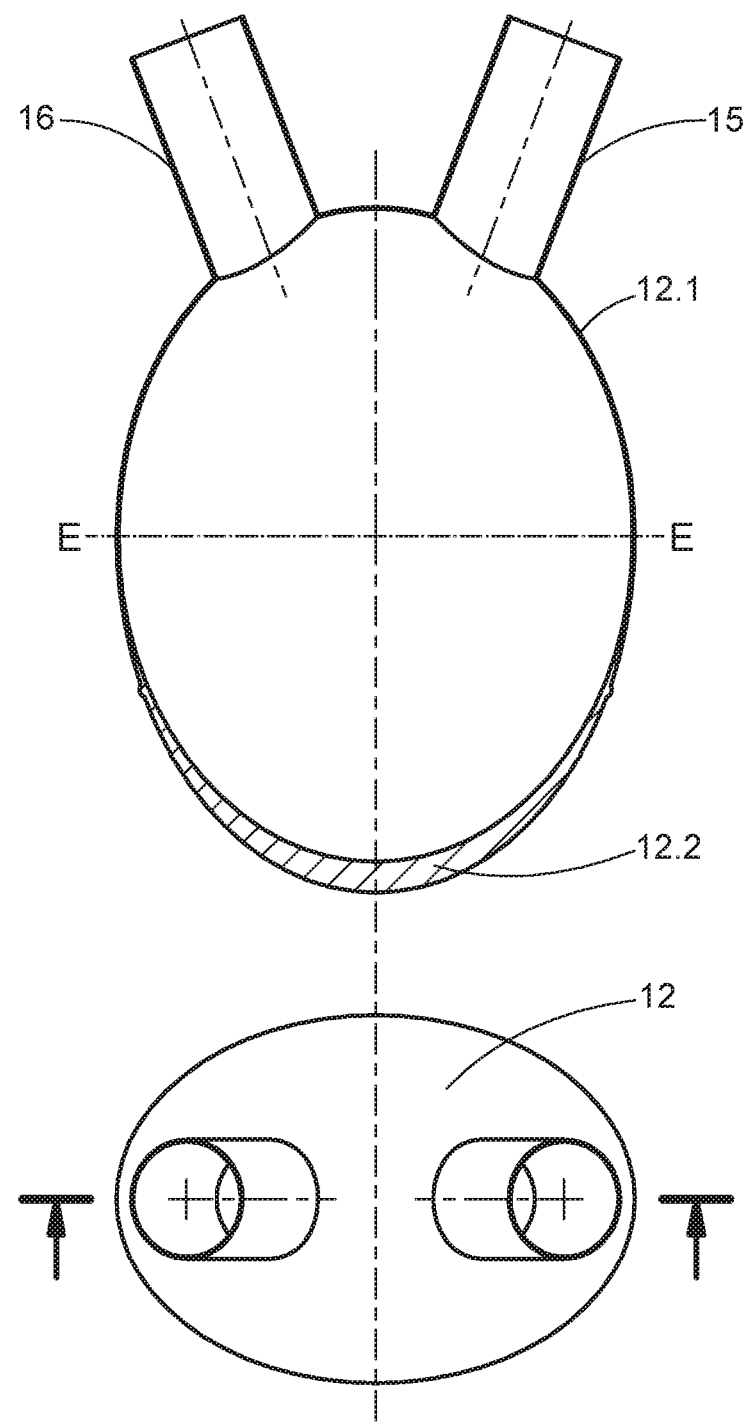

FIG. 18 a seamless blood bag with thickened lower half like a sickle or a parabola.

Figure 19:
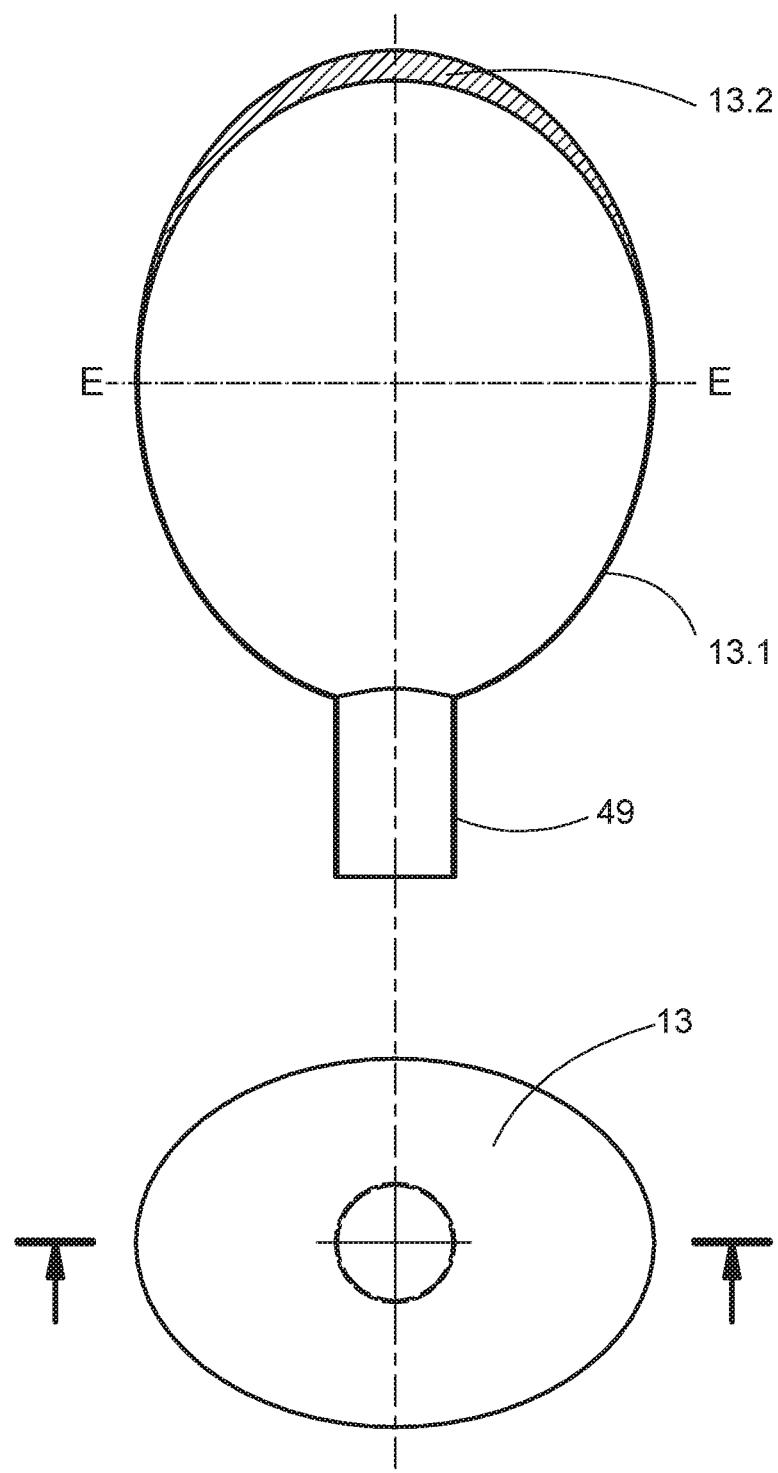

FIG. 19 a seamless drive bag with thickened upper half like a sickle or a parabola.

Figure 20:
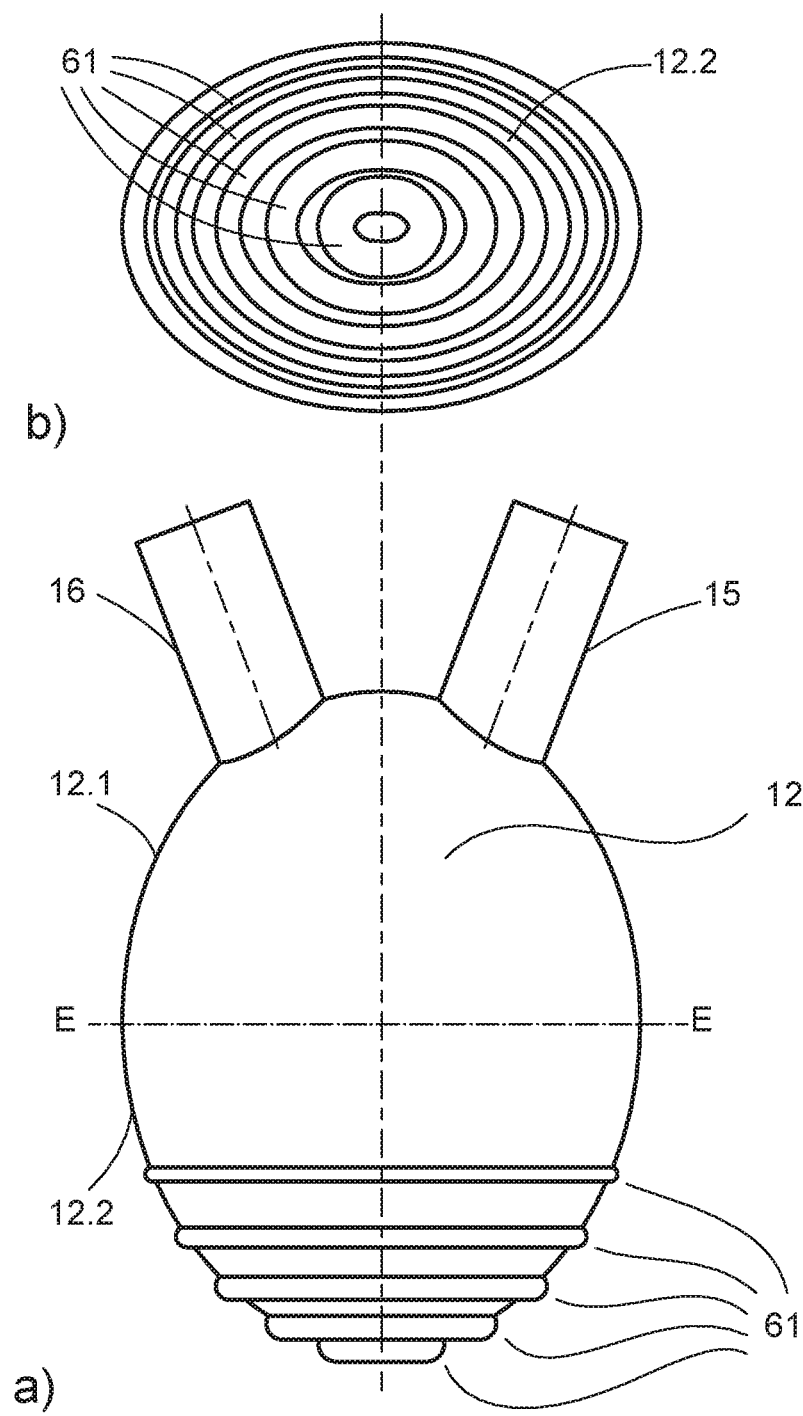

FIG. 20 a seamless blood bag with geared lower half.

Figure 21:
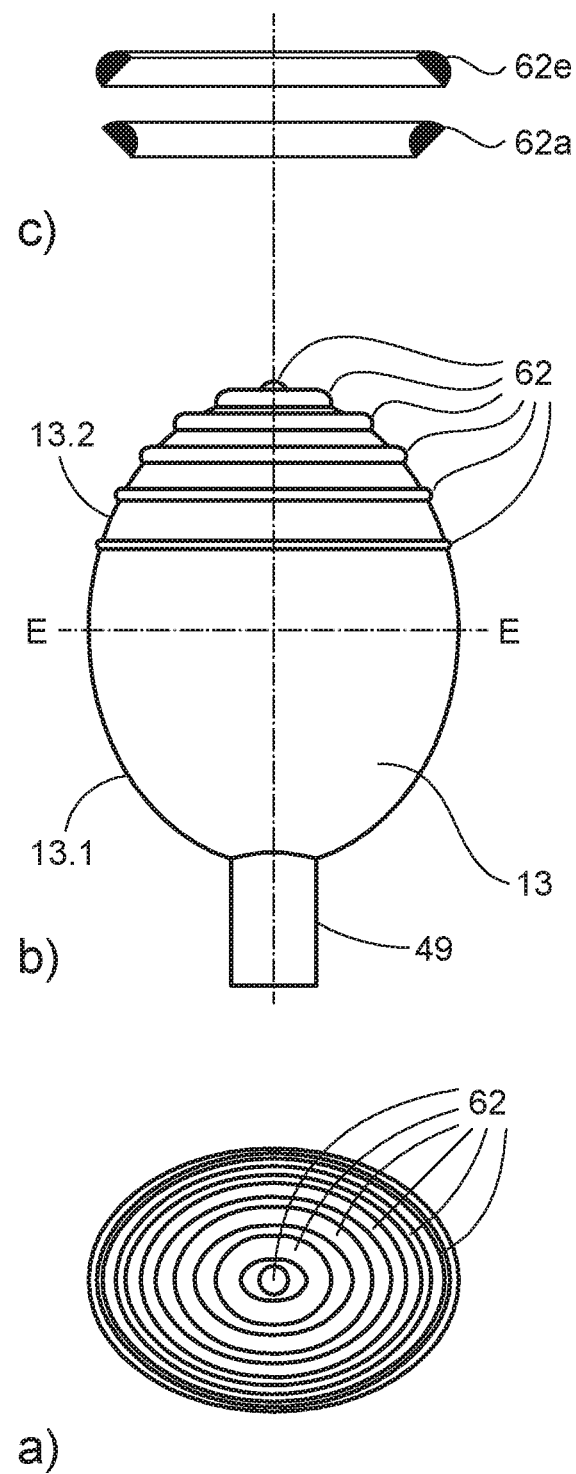

FIG. 21 a seamless drive bag with geared upper half.

Figure 22:
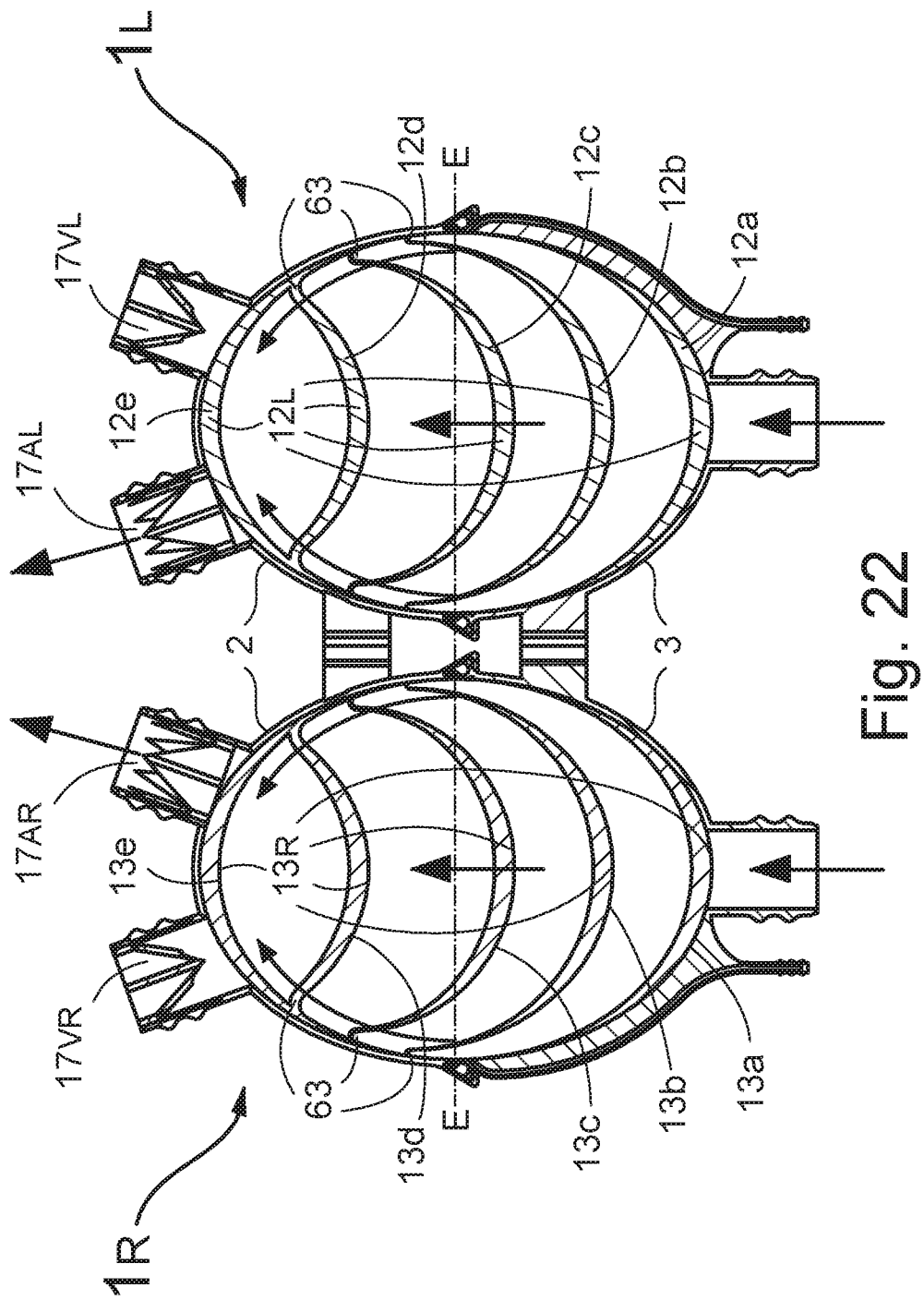

FIG. 22 an artificial heart with like a parabola thickened blood bags beating synchronously in the systolic phase.

Figure 23:
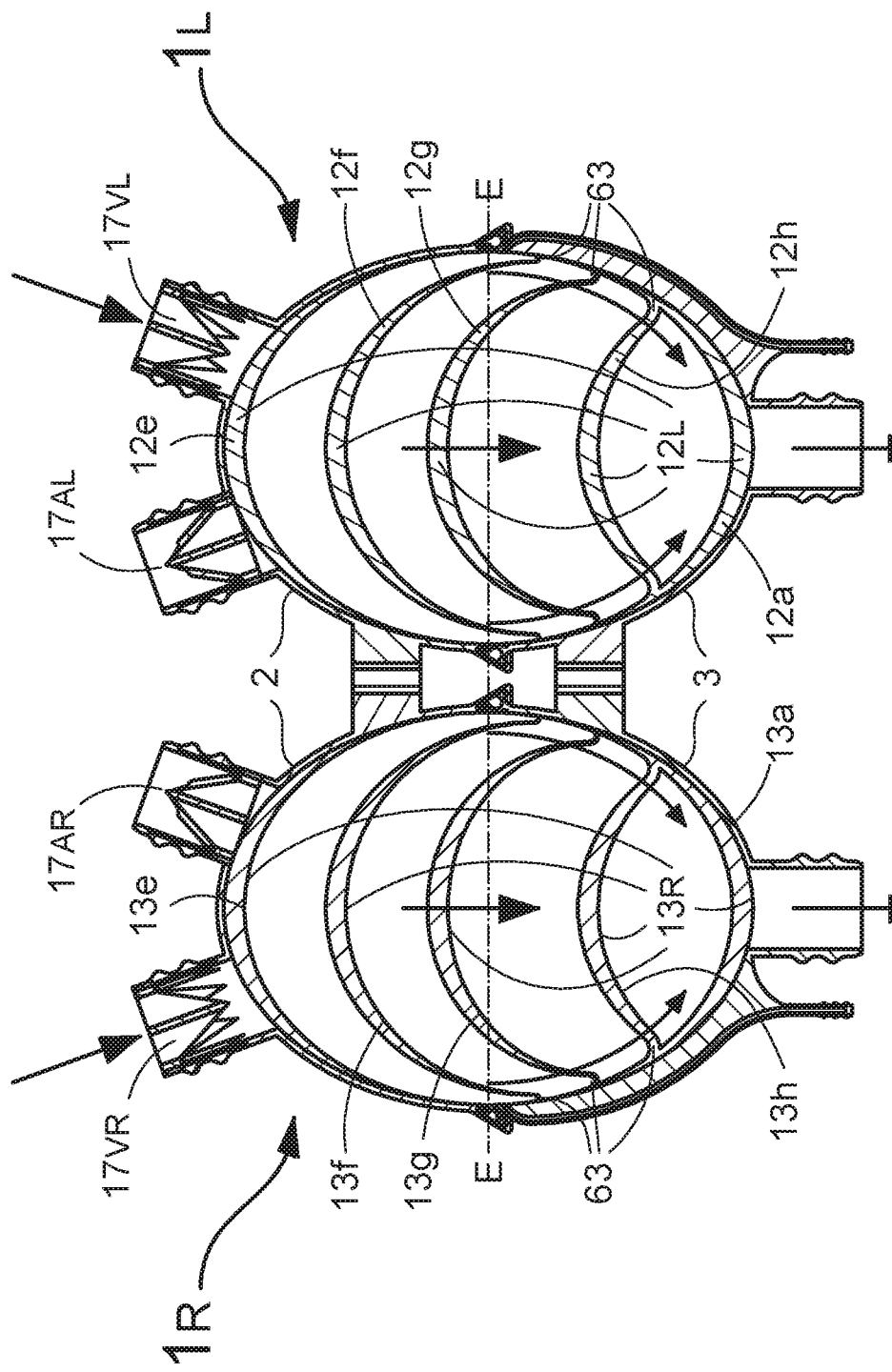

FIG. 23 an artificial heart with like a parabola thickened blood bags beating synchronously in the diastolic phase.

Figure 24:
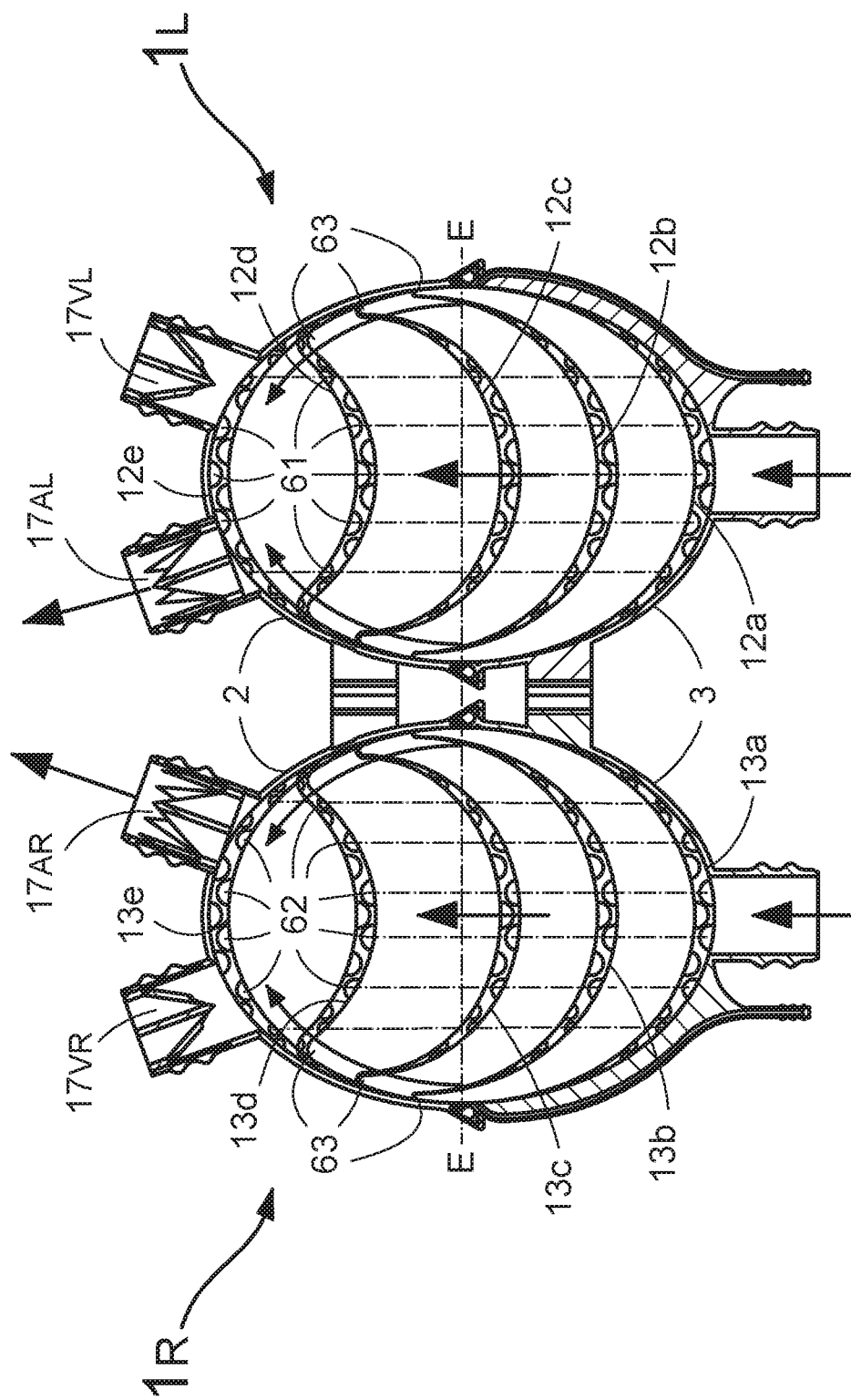

FIG. 24 an artificial heart with geared blood and drive bags beating synchronously in the systolic phase.

Figure 25:
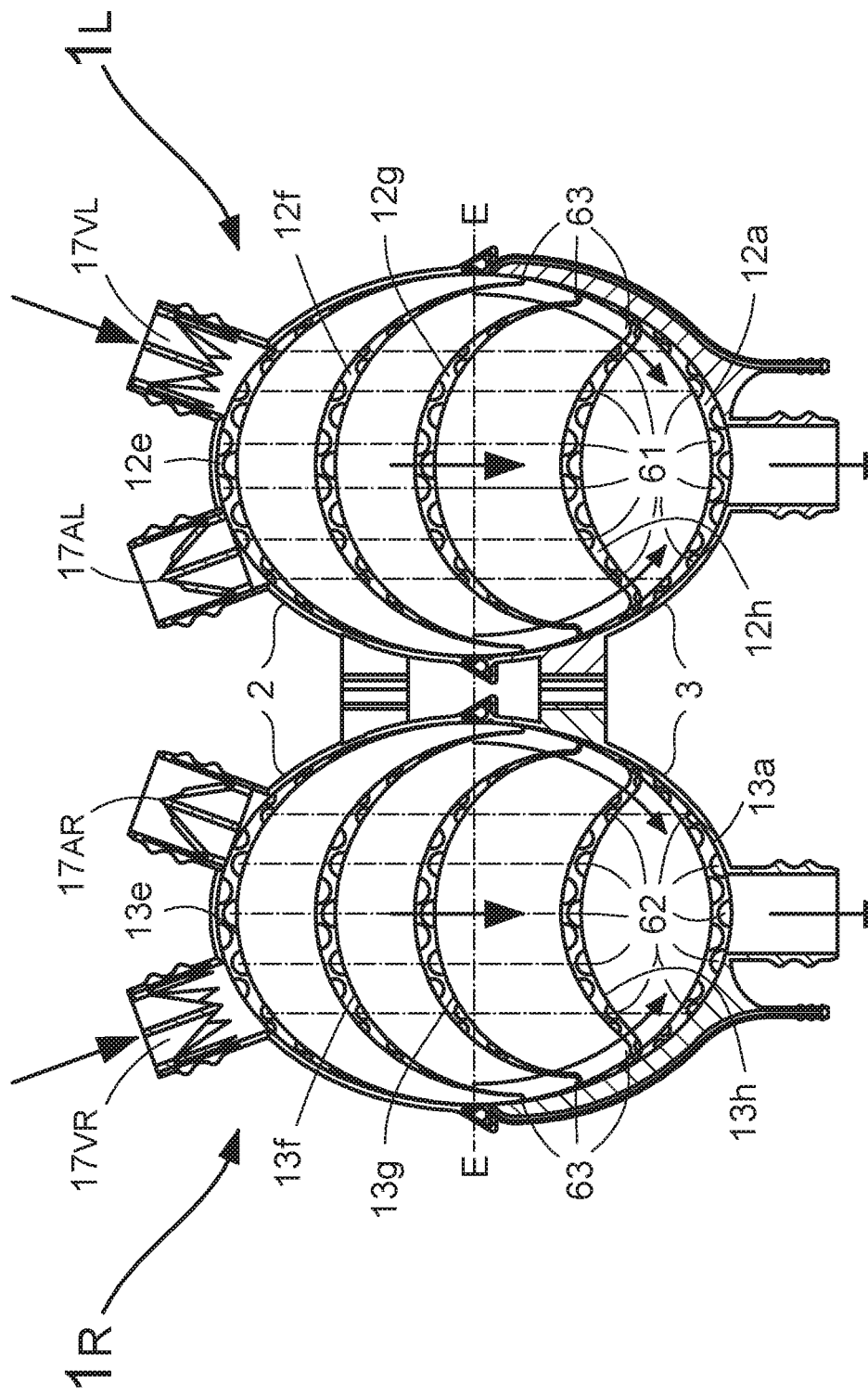

FIG. 25 an artificial heart with geared blood and drive bags beating synchronously in the diastolic phase.

Figure 26:
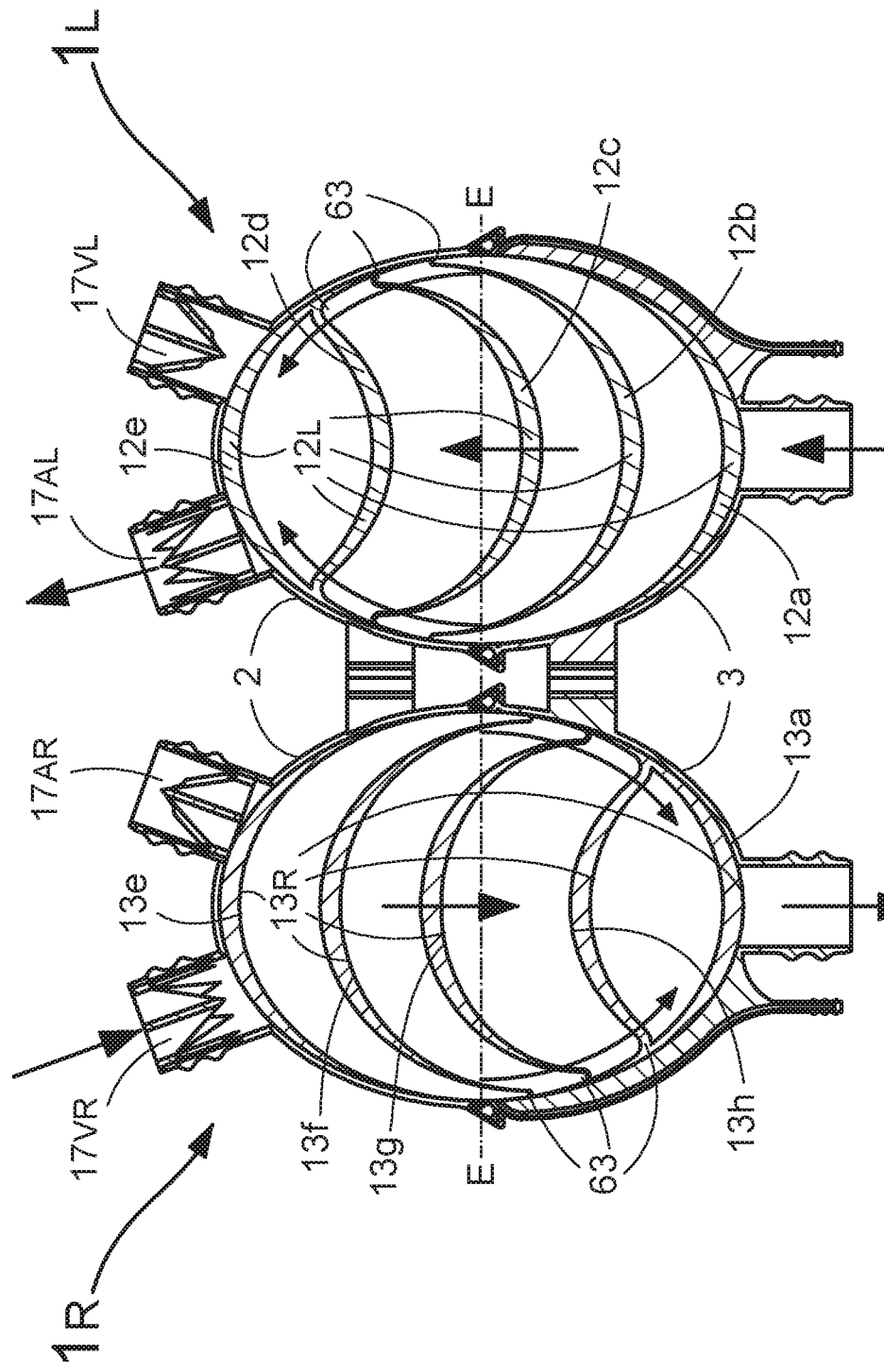

FIG. 26 an artificial heart with like a parabola thickened blood bags beating asynchronously in the systolic phase.

Figure 27:
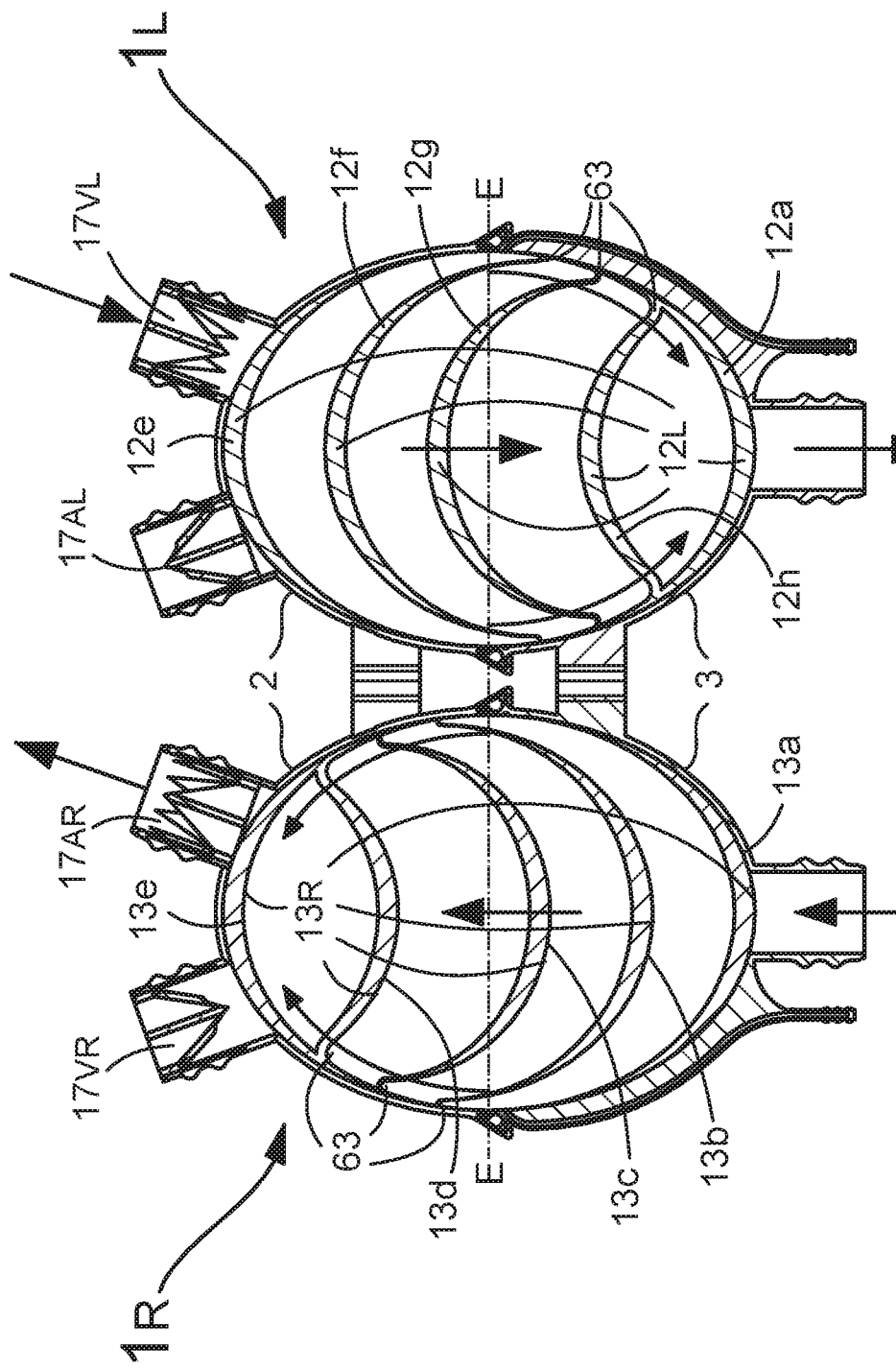

FIG. 27 an artificial heart with like a parabola thickened blood bags beating asynchronously in the diastolic phase.

Figure 28:
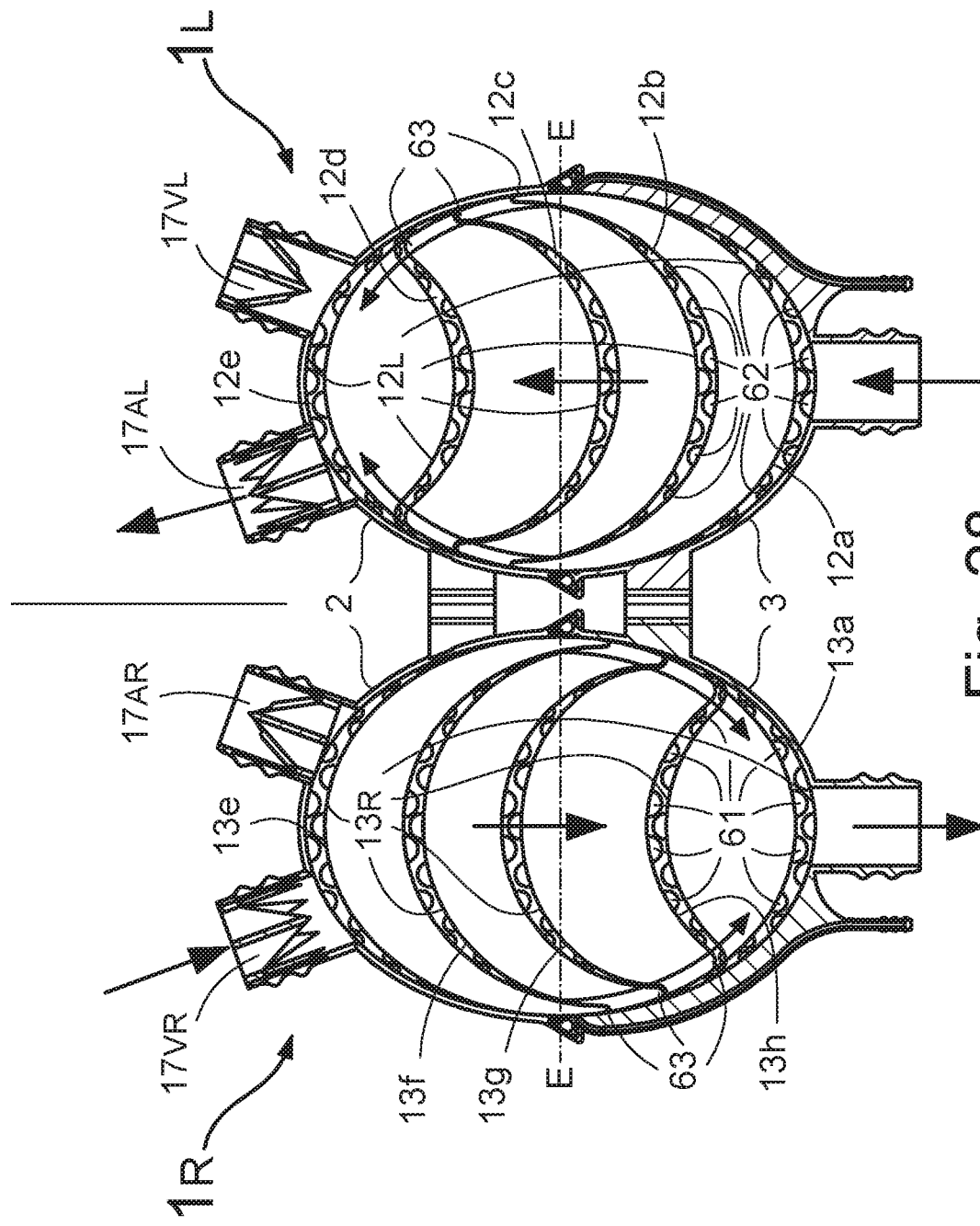

FIG. 28 an artificial heart with geared blood and drive bags beating asynchronously in the systolic phase.

Figure 29:
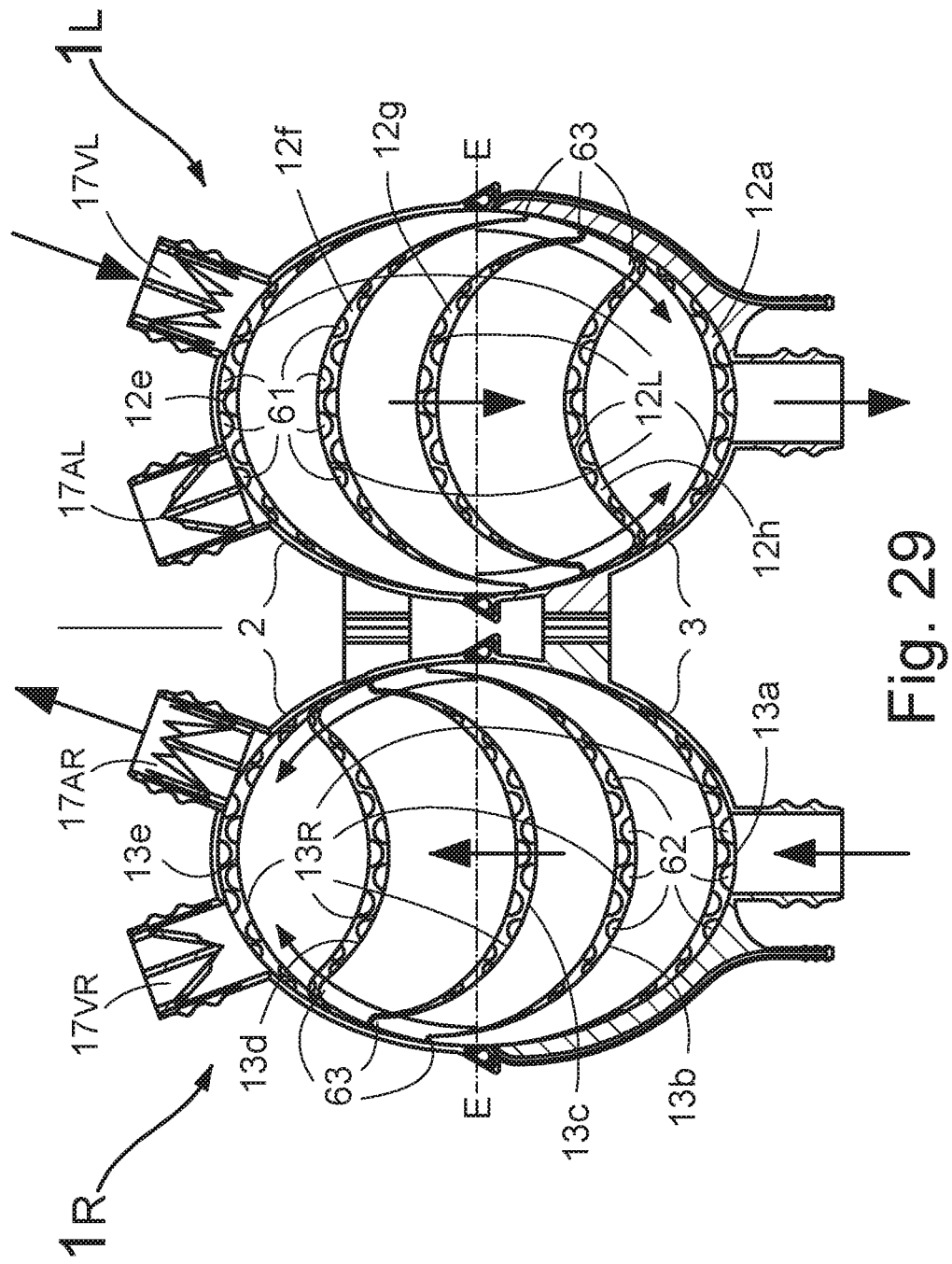

FIG. 29 an artificial heart with geared blood and drive bags beating asynchronously in the diastolic phase.

Figure 30:
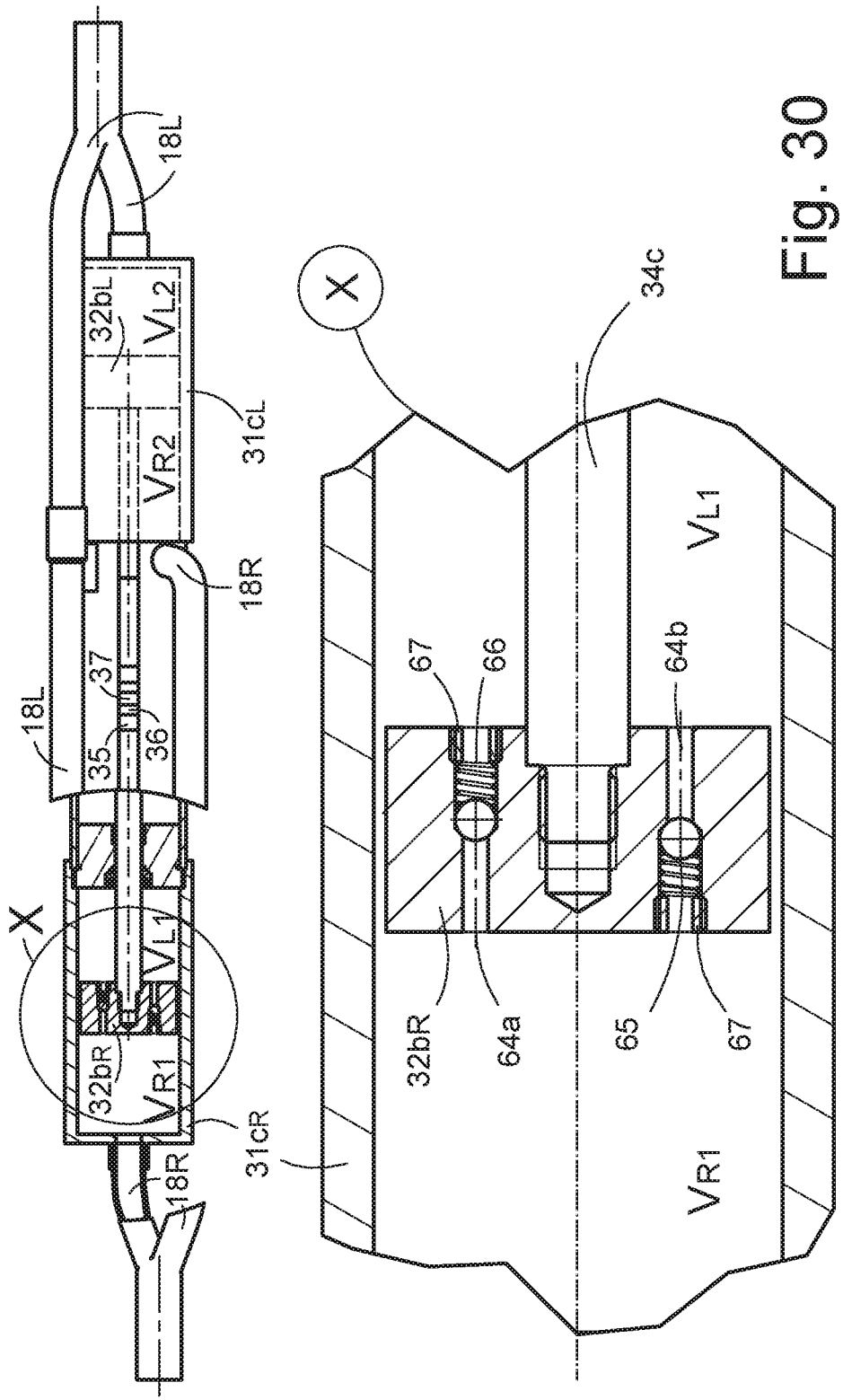

FIG. 30 a double-piston pump unit consisting of a piston rod with a piston on its both ends without sealing. Each piston has a case with a cylindrical working chamber and a relief valve on each side.

The number of identical parts is always the same. Indices with letters designate different versions or sizes of the same element. The reference of the letters is as follows:

A: Artery L: left side of the patient
V: Vein R: right side of the patient

DETAILED DESCRIPTION OF THE INVENTION

Figure 1:
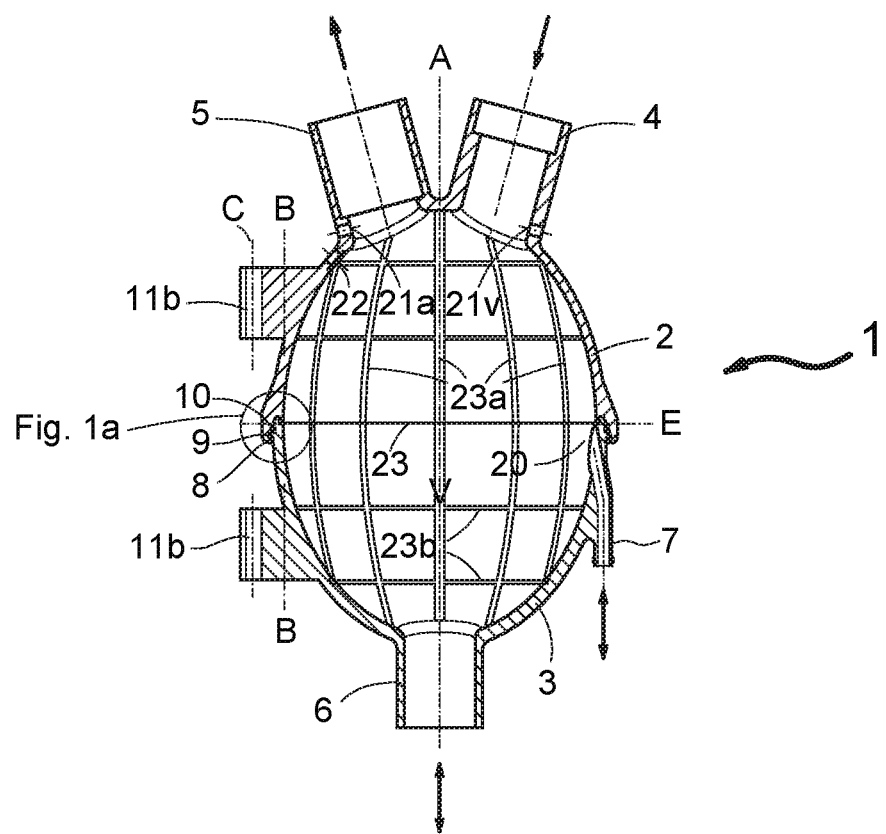
FIG. 1 a longitudinal section through a three-dimensional elliptically designed hard shell of an artificial half of a heart, composed of two half shells.
Figure 1A:
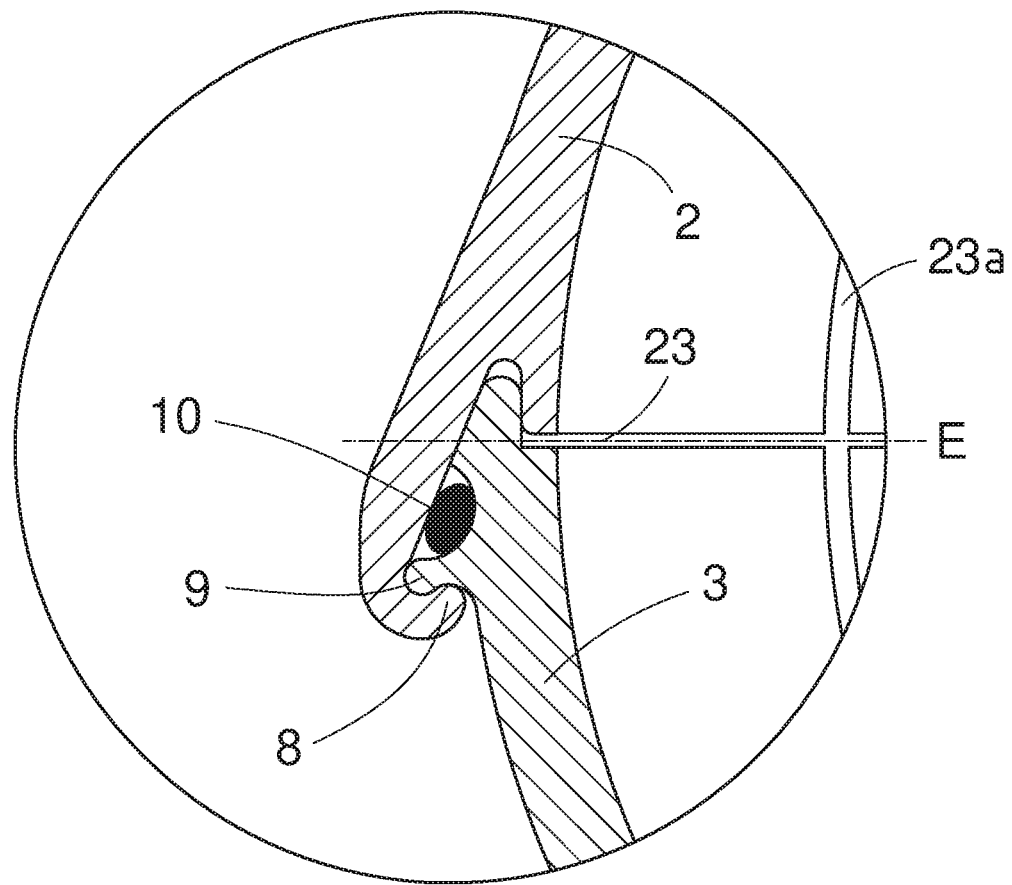
FIG. 1a the details of the plug connection of the two half shells of one half of the heart including its seal.

According to FIG. 1, the hard shell of one half of the heart (1) disposes of the geometrical shape of a three-dimensional ellipsoid, so that the section through plane (E) vertically to the longitudinal axis (A) represents a flat ellipse. The hard shell of a half of the heart is preferably composed of two half shells, the upper half shell (2) with the inlet (4) as well as the outlet (5) opening for blood, and a lower half shell (3) with inlets and outlets for drive medium (6) and for lubricating and regulating agent (7) for cardiac output (V). The upper and lower half shells with their connectors preferably consist of biologically compatible plastics, produced by injection molding or three-dimensional printing, with polished surface and preferably coated by precious metal. At their free elliptic edges close to plane (E), they feature, as shown enlarged as a detail in FIG. 1*a*, positive and negative shapes with a preferably conically slanted surface, which during assembly are placed on each other. Centrally on one of the conically slanted surfaces of the interface of the two half shells, a groove is located comprising a sealing ring (10), preferably an O-ring, which hermetically seals the two half shells with respect to air and liquid.

During the assembly of the two half shells (2 and 3), the lower edge (8) of the upper half shell (2) is inserted over the edge (9) of the lower half shell (3), tightly being pressed against the elliptical edge all around.

On the central plane of the heart (C), the two half shells (2 and 3) feature a pluggable elastic double connector, composed of two cylinders (11*a* and 11*b*) placed over each other, positive respectively massive, and negative respectively hollow, enabling to position two identical halves of the heart rotated by 180° with respect to the central plane of the heart (C) and establish an interlocking connection between them. This way a whole artificial heart is combined. Narrowing the connecting straps along the axes (B) forms a film joint, which increases the elasticity and flexibility between the two halves of the heart. This enables the two halves of the heart to be adapted to the individual curvature of the chest and to remain movable with respect to each other within the body.

The half of the heart illustrated here represents the left half of an artificial heart. Rotation by 180° around the axis of one of the straps (11*a* and 11*b*) converts it into the right half of the heart. Inside the inlet (4) and the outlet opening of the blood (5) one step each is provided intended for accommodation of the valve, a hole (21*a* and 21*v*) for integration of a miniature camera of an optical sensor or a light or laser light reflecting system, for signal transmission e.g. through glass fibers for monitoring and remote diagnosis of the valves when used as artificial heart valves.

The inlet and outlet of the lubricating and regulating agent (7) enters at hole (20) into the interior of the half of the heart (1), preferably into the lower half shell (3) and into the oval ring gap (23) between the two half shells (2 and 3). From that position, the lubricating and regulating agent is distributed to the longitude- and latitude-shaped grooves (23a and 23b) on the inner surface of the two half shells and between the two bags, blood and drive bag. The hole (22) within the upper half shell (2) is used for attachment of a pressure sensor measuring the blood pressure directly at the location when it is built up, within the blood chamber, and transmitting the result by signal line to the central control unit.

Figure 2:
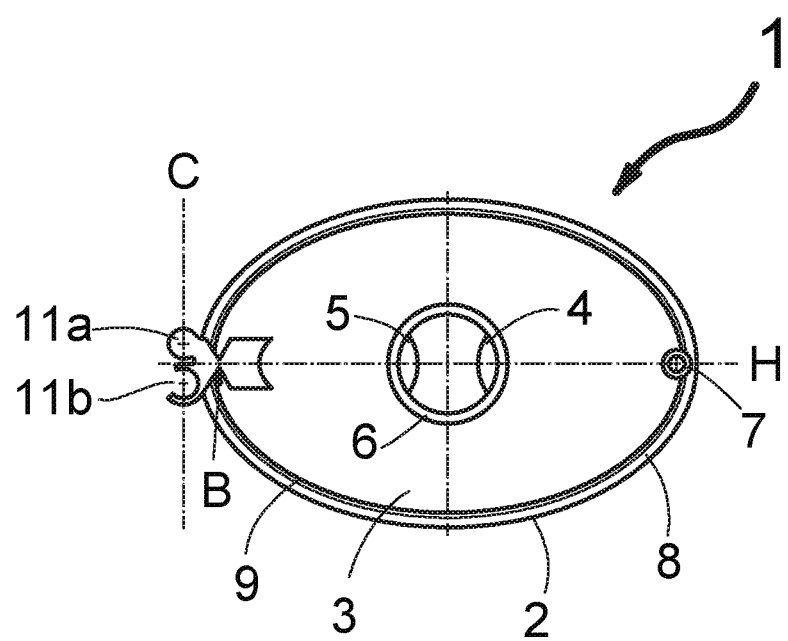
FIG. 2 the view from below to the left half of the heart shown in FIG. 1 with a film joint (B) and two positively and negatively shaped fasteners.

FIG. 2 shows the bottom view of the left half of the heart. The outer ellipse represents the contour of the upper half shell (2), which by its edge (8) grasps behind the edge (9) of the lower half shell (3). See FIG. 1A. Parts of the blood entry (4) and outlet opening (5) are visible through the connector (6) of the lower half shell (3).

Connector (7) is shown at the right side of FIG. 2, at the bottom of half shell (3) on plane (H). The hole of this connector (7) leads tangentially into the elliptic groove (23) between the two half shells (2 and 3) in the interior of the half of the heart, and is used for supply and discharge of a lubricating agent like paraffin, which ensures tightness and suppleness of the two bags, which reduces their mutual friction and regulates the cardiac output.

The left side of FIG. 2 shows on the central plane (C) of the heart at each half shell (2 and 3) a pluggable elastic double connector (11a and 11b), consisting of a narrowing as a film joint (B), and two preferably cylindrically positive (11a) and negative shaped (11b) fasteners.

Figure 3:
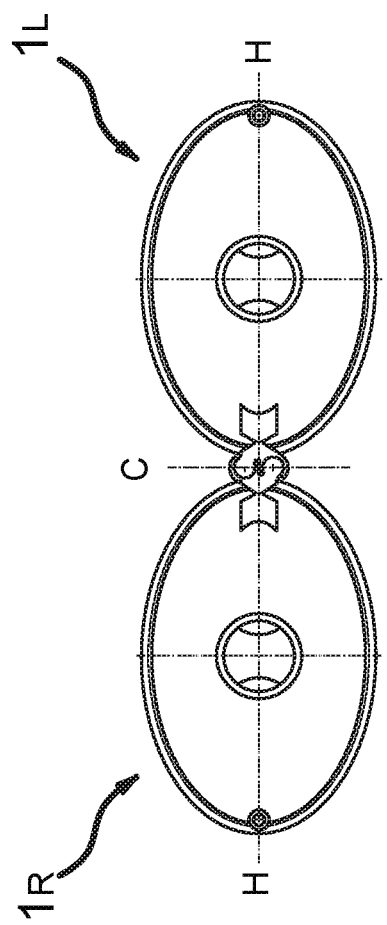
FIG. 3 bottom view of two equal halves of the heart (1R and 1L) assembled by fasteners to form a complete heart.

FIG. 3 shows the bottom view of two identical halves of the heart (1R and 1L). These two identical halves are mutually rotated by 180° with respect to the central plane of the heart (C), and assembled to an entire heart by insertion of the positive (11a) into the negative (11b) fasteners.

Figure 4:
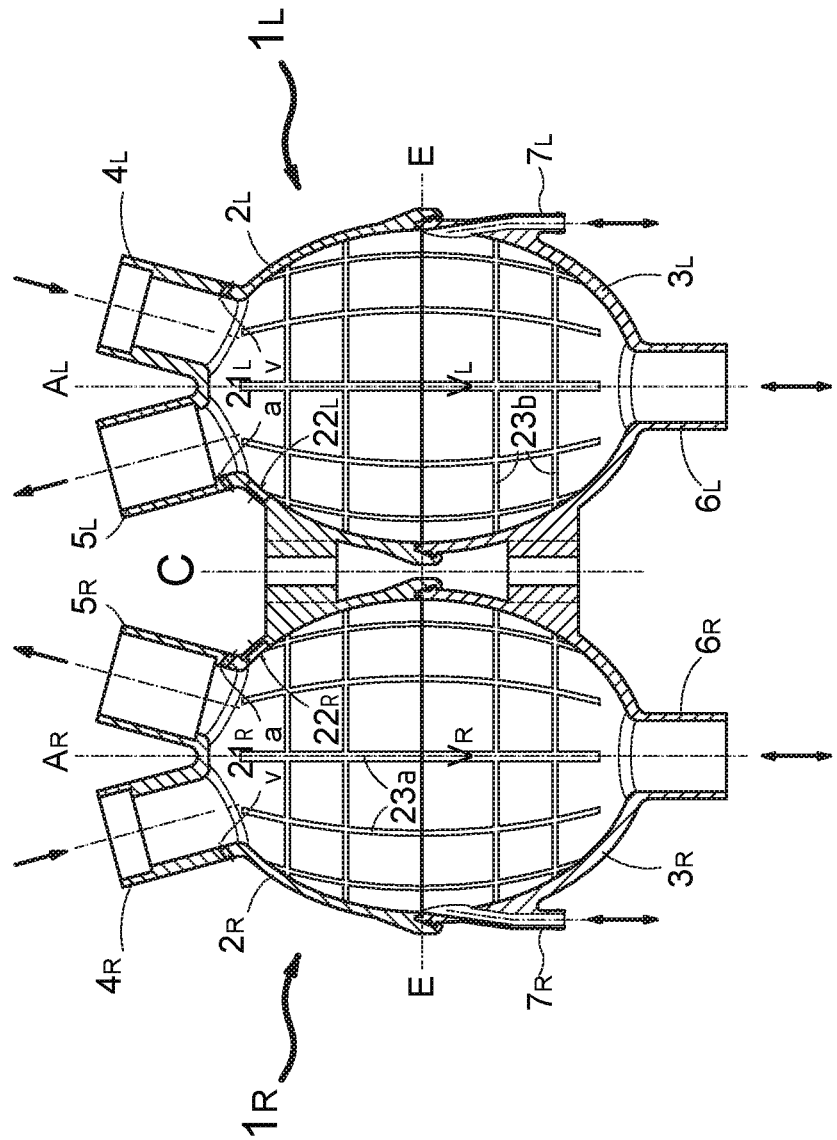
FIG. 4 a longitudinal section through the two identical halves of the heart (1R and 1L) along the plane (H) of FIG. 3.

FIG. 4 shows a longitudinal section through the hard shells (1R and 1L) of the two halves of a complete artificial heart. The two identical halves are assembled by mutual connection of their positive and negative fasteners (11a and 11b), rotated by 180° with respect to the central plane of the heart (C).

Figure 5A:
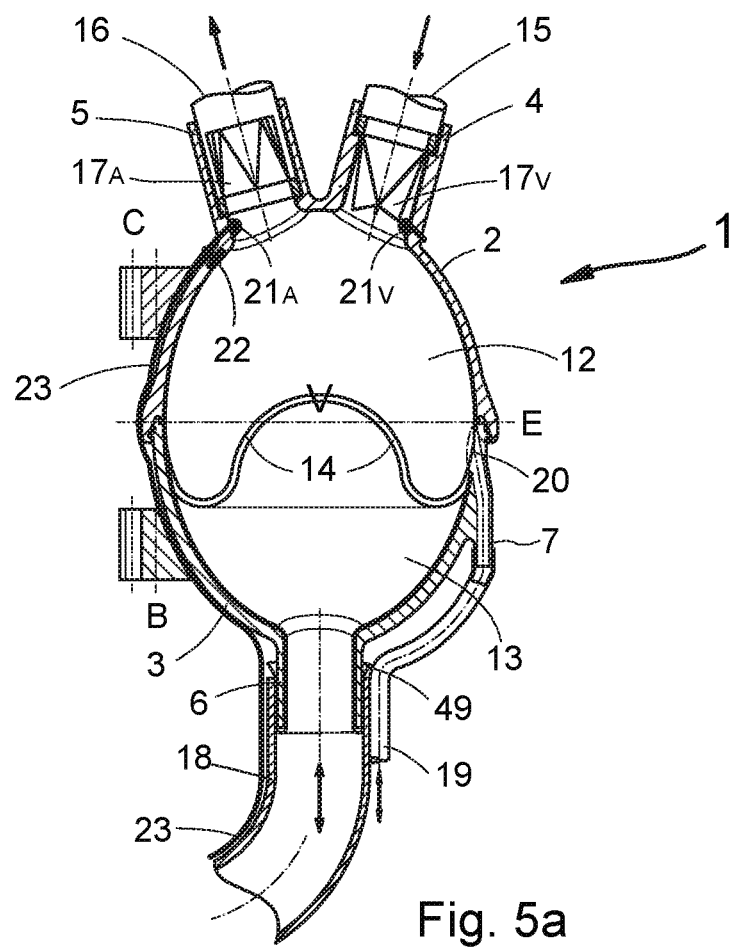
FIG. 5a one half of the heart (1) equipped with blood and drive bags (12 and 13), the two valves (17A and 17V) replacing the heart valves, two optical sensors (21A and 21V) and a blood pressure sensor (22).

FIG. 5a shows one half of the heart (1) composed of the two hard half shells (2 and 3) in a longitudinal section. The upper half shell (2) features the blood chamber (12) with the two in- and outlets (15 and 16). The blood chamber (12) consists of a very elastic material like silicone or polyurethane, but preferably it is woven from biologic fibers like threads from spiders or silkworms. From this very tensile strength material and highly elastic material, a blood chamber is woven in the form of a bag with the volume of the half of the heart (V) together with the two in- and outlets (15 and 16) as sleeves of the blood bag, preferably in one piece, and inserted into the upper half shell (2), when it is in opened state.

It is also possible to stick the blood chamber within its entire or a partial range, i.e. above the equator level (E), to the inner surface of the half shell, so that it is not folded during its work and does not detach cameras (21A and 21V) and pressure sensor (22) from the wall. Within the blood entry and outlet openings of the blood chamber (15 and 16), valves (17A and 17V) are installed as artificial heart valves in a manner, so that the material respectively the tissue of the in- and outlets, the sleeves (15 and 16) are clamped together with them between the heart valves and the openings (4 and 5) of the upper half shell (2). The in- and outlets of the blood chamber protrude from the hard half shell (2) sufficiently to be sewed directly on the corresponding veins and arteries, or on extension lines and/or to be connected by a clamping and/or screw and/or adhesive connection. In the in- and outlets of the upper half shells, preferably at the end of the blood chamber in front of the valves, cameras (21A and 21V) or optical sensors and a pressure sensor (22) are installed. Their cables are guided in parallel to the supply hoses (18 and 19) from the chest towards outside to the control unit.

The lower half shell (3) contains the pressure and suction chamber (13), which is manufactured together with its sleeve (49) in one piece like the bags, consisting of tensile strength material and very elastic material like silk or plastic threads. Its shape and volume corresponds to the half of the heart (1). This chamber (13) is usually up to the half glued on the inner wall of the lower half shell (3). By means of a connector (6) and a hose (18) it is filled with a liquid medium similar to blood plasma and compatible to the blood. It is possible to make use of saline or coconut milk as drive medium.

A pump unit, preferably placed outside the body, attached on the chest or on a corset, pumps the drive medium through an elastic hose (18) to the connector (6) into the drive chamber (13). The bag or balloon of this drive chamber presses onto the bag or balloon of the blood chamber (12), pushing the blood through the left valve (17A) located at the left half of the heart (as shown here) into the aorta or into the pulmonary artery at the right half of the heart. The valve (17V) of the pulmonary vein at the left half of the heart or of the cava veins at the right half of the heart meanwhile closes automatically. When the drive medium from the drive chamber (13) by means of the pump unit is expulsed, a suction is created in the intermediate space (14) between blood and drive chamber. This suction draws the blood chamber towards the drive chamber, increasing its volume. This effect closes the valve (17A) and simultaneously opens valve (17V), so that the oxygen-rich blood of the lungs flows into the blood chamber.

Within the intermediate space (14) between blood and drive chamber as well as in the longitudinal and transversal grooves (23a and 23b) at the inner surface of the hard shell, a lubricant like paraffin is provided, intended to reduce the friction between the two chamber walls and the hard half shells (2 and 3), thus extending the lifetime of the material of the two chambers and the threads of the bags, and keeping them in a dense and supple state. The filling quantity of this lubricant determines the cardiac output of the half of the heart and ensures its variability at constant pulse rate. Regulation of filling quantity and exchange of lubricant takes place by means of connector (7) and hose (19). The hole (20) of connector (7) leads to the intermediate space (14) between the two blood and drive chambers and to the oval ring gap (23) between the two half shells (2 and 3) on plane (E). From that position, the lubricant is distributed within the grooves (23a and 23b) and between the two blood and drive chambers.

By means of elastic hose (19), the connector (7) is connected to hose (18), which is guided through an opening in the chest from the inside of the body towards the outside to a storage tank located in the case of the pump and control unit.

One half of each bag (12 and 13) always adheres to the inside of the half shells (2 and 3). The other loose halves of the bags are placed back to back, moving rhythmically up and down together.

Figure 5B:
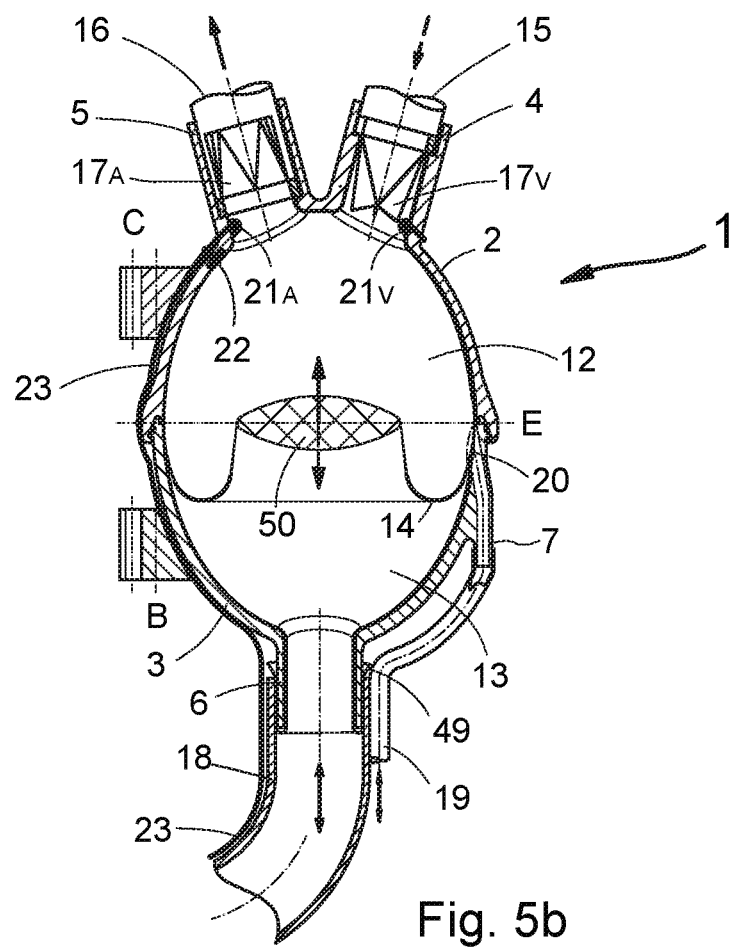
FIG. 5b one half of the heart (1) equipped with blood and drive bags (12 and 13), the two valves (17A and 17V) replacing the heart valves (1), furthermore two optical sensors (21A and 21V) and a blood pressure sensor (22). The tips of the free and movable halves of the blood and drive bags are connected to a lenticular pad (50), which moves up and down between its two end positions, in parallel to itself and covering every time at the end of its movement, the connecting bores of the half shells.

FIG. 5b shows a longitudinal section of one half of a heart (1), composed of two hard shells (2 and 3), with a lenticular and elliptically shaped pad (50) filled with a gel like paraffin or medical silicone placed between the two movable halves of the bags located back to back. The pad is placed centrally and perpendicularly to the longitudinal axis (A) of the half of the heart. Guided by the threads of the two halves of the bags, the gel pad (50) permanently moves parallel to itself like a piston without rod. In its final positions, it closes the openings of the hard shells, in order to prevent the penetration of a part of a bag or balloon into these openings or into a valve. The material and the threads of the two bags are always unstressed and unloaded; no tensile stress, pressure or torsion acts on them. They always float up and down respectively forth and back between the two liquids together with the current. The forces acting on the two faces of the bags are always nearly identical. This enables a maximum biological lifetime of the materials used to be achieved.

Figure 5D:
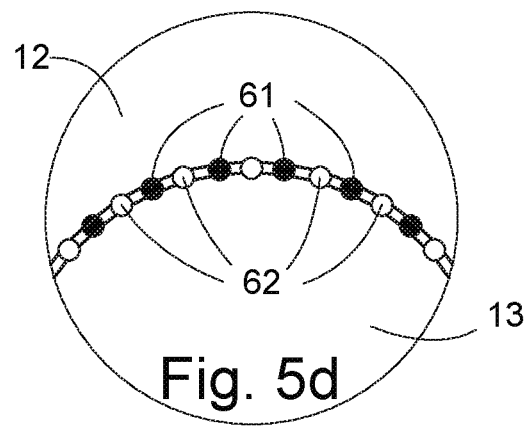
FIG. 5d a partial section of the halves of the blood and drive bags placed on each other (12 and 13) with projecting bulges (61 and 62)
Figure 5C:
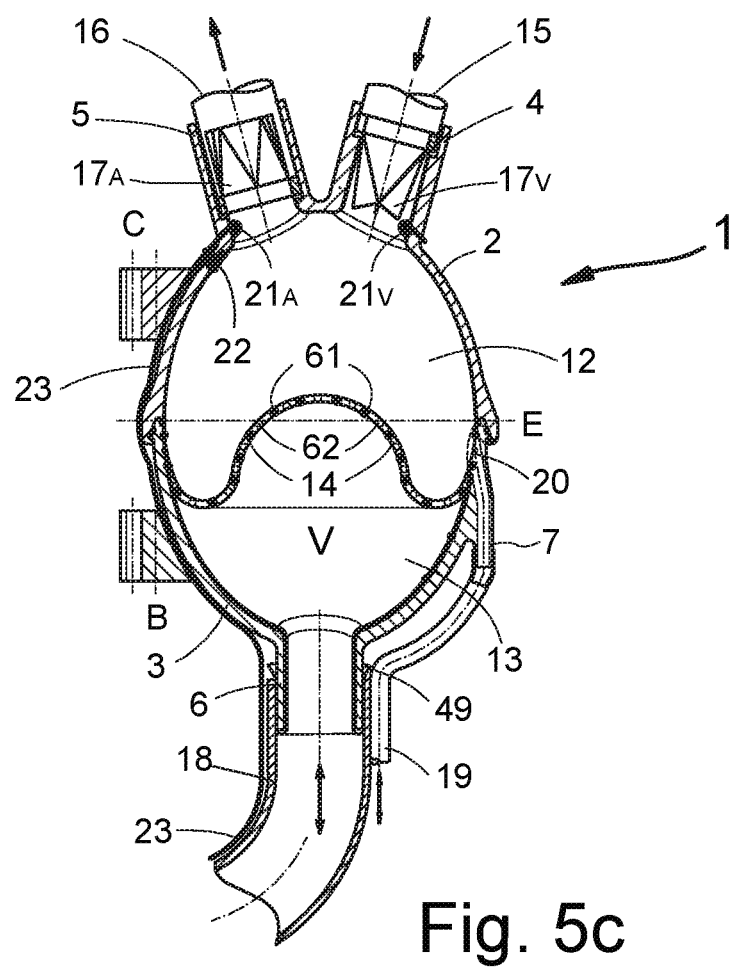
FIG. 5c one half of the heart (1) with the halves of the blood and drive bags placed on each other (12 and 13) featuring ring-shaped or elliptical bulges.

FIG. 5*c* shows one half of the heart as described in FIG. 5*a*. The rear face of the halves of the drive and blood bags (12 and 13) placed on each other, features circular or elliptic bulging or reinforcement rings (61 and 62) in form of teeth, which are produced during 3D print of the bags from plastics, or by insertion of tooth-shaped non extensible rings consisting of plastics or spring steel into the tissue during the weaving process of the bags. In normal cut, the shape of the teeth may appear like an arc of a circle (as illustrated here), but cycloid, involute or simpler shapes are possible as well. The bags this way become a toothed bag up to the half. This way, the outside of the bags is equipped with gear-shaped non extensible circular or elliptic rings (61 and 62), which are bended over together starting from the first bulging at the cardiac apex up to the valves (17A and 17V), tooth into tooth gap, thus creating together a migrating wave. The tooth rings migrate together link by link along the wall of the half shells (2 and 3) up to the equator; then they are placed at their intended positions at the wall of the half shells like the parallels of latitude on a globe, without being stretched or folded. These rigid teeth respectively rings (61 and 62) also prevent penetration of the end of the bags into the openings of the halves (4, 5 or 6) of the heart.

FIG. 5*d* shows a small section of the two blood and drive bags (12 and 13) placed on each other, here provided with a simple lantern gear toothing circular in normal cut. The chain with the black links respectively teeth (61) represents the cut through the blood bag (12), the chain with the white links respectively teeth (62) the cut through the drive bag (13).

Figure 6:
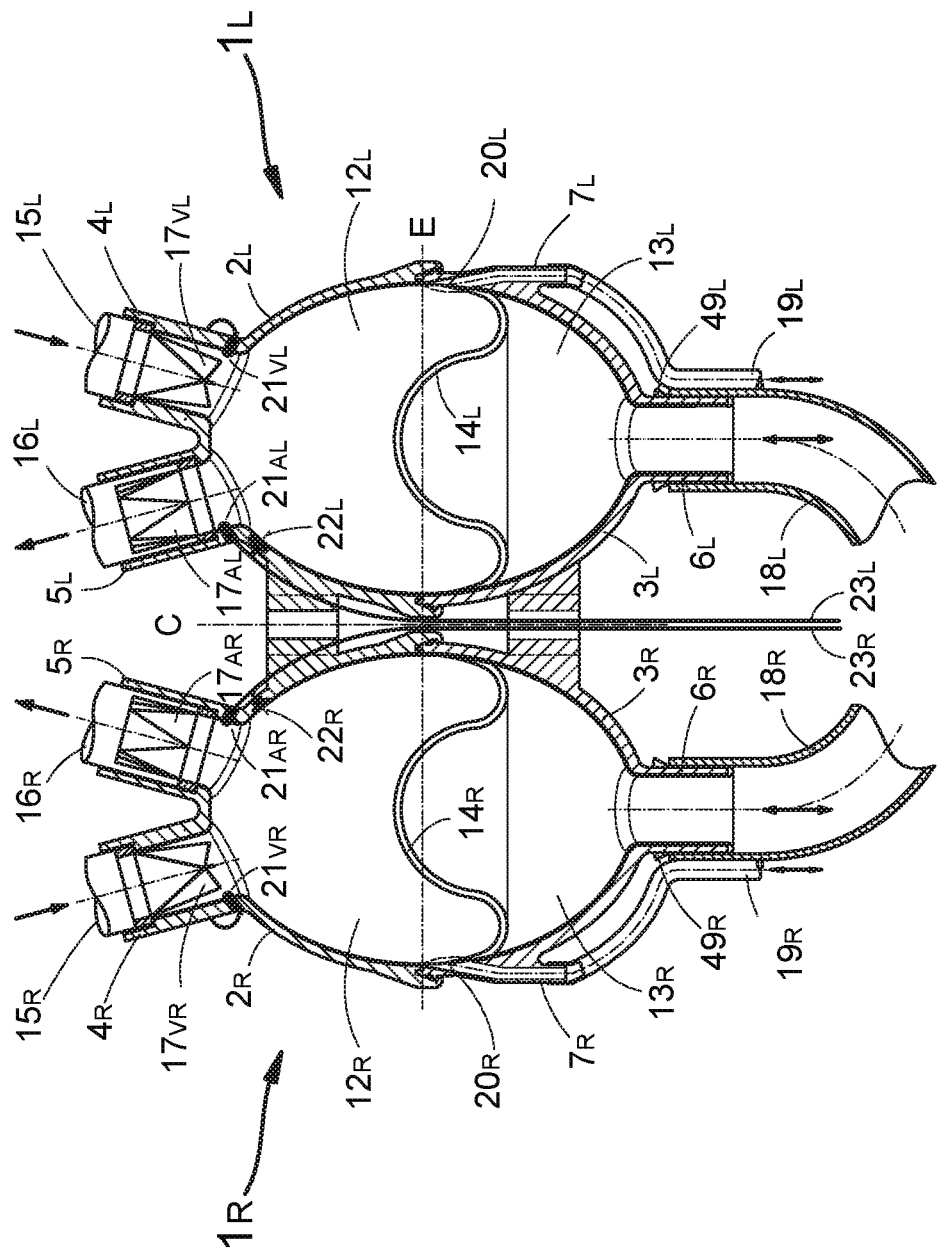
FIG. 6 an entire artificial heart, composed of two identical halves (1R and 1L).

FIG. 6 shows a longitudinal section of an artificial heart according to the invention, composed of two identical halves (1R and 1L). The upper zone contains from the left to the right the valves (17VR, 17AR, 17AL and 17VL) replacing in turn the tricuspid valve, the pulmonary valve, the aortic valve and the mitral valve. Connectors (7R, 6R, 6L and 7L) with supply lines (19R, 18R, 18L and 19L) for lubricating and driving agent are provided in the lower zone. These supply lines are guided together with the cables (23R and 23L) of cameras (21VR, 21AR, 21AL and 21VL) and blood pressure sensors (22R and 22L) from the chest towards outside and connected to the pump and control unit outside the body.

Figure 7:
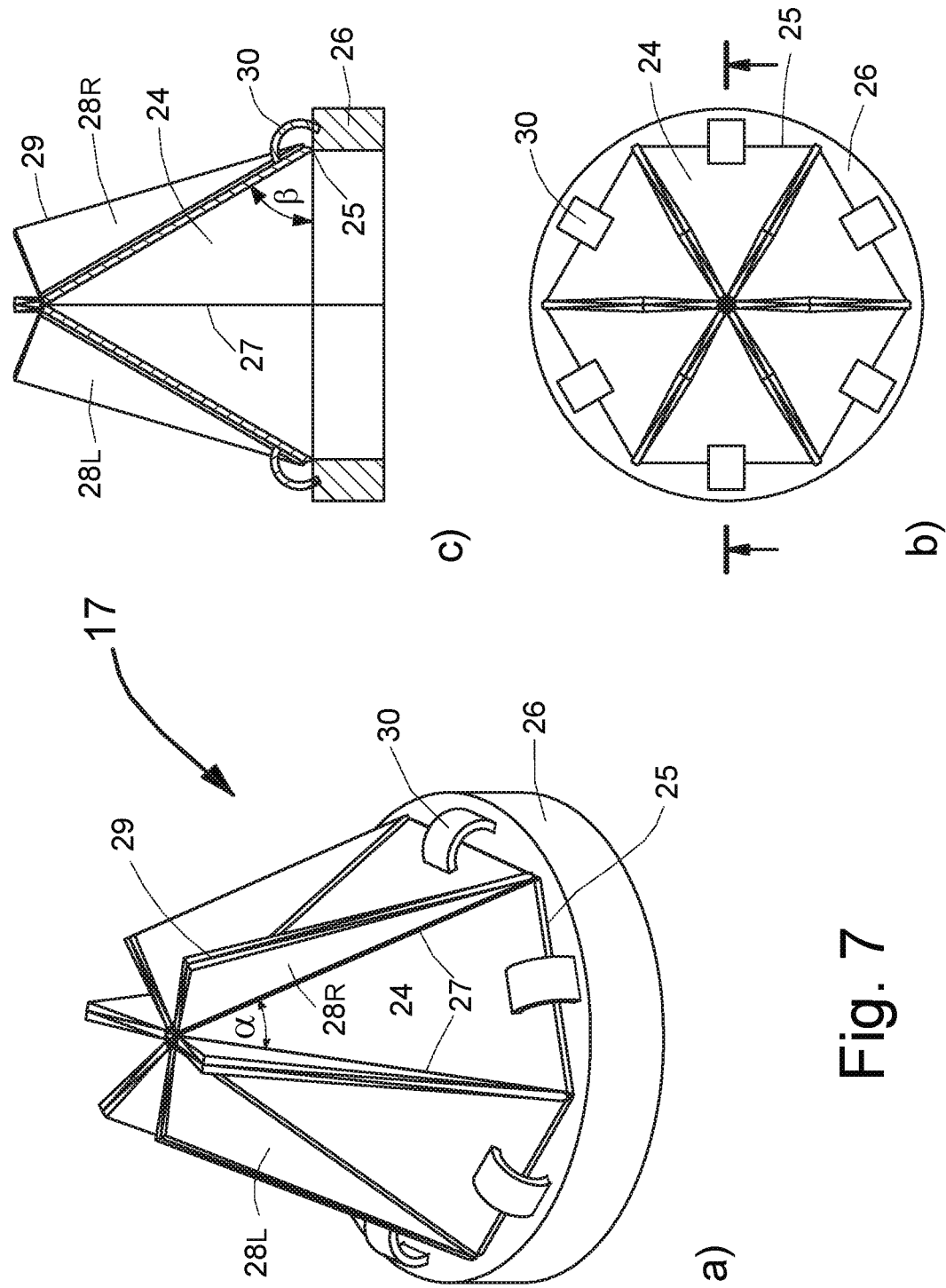
FIG. 7 an artificial check valve with six blades as valve flaps in closed state, used for the artificial heart as replacement for a heart valve, in three views (a, b and c).

FIG. 7 shows three views (a, b and c) of a closed valve (17) according to the invention, acting as artificial heart valve. The valve consists of (n), at least three or more, preferably six thin lamellae (24) consisting of solid material like plastics, in round configuration attached by film joints (plastic joint) (25) in a swiveling manner to a polygonal hole of the valve ring (26). The valve lamellae (24), also called main blades, are triangular-shaped with two sides (27) of equal length, an intermediate acute angle ($\alpha$) and a shorter side (25) opposed to this acute angle, formed as a joint e.g. a film joint. Angle ($\alpha$) is usually lower than 1/n of 360°, with (n) designating the number of lamellae. Each valve lamella (24) is inclined with respect to the plane of the valve ring (26) from ca. 90° in opened state, to a value of ($\beta$) in closed state. The latter value amounts to a value preferably to be selected between 45° and 60° to ensure safe function and long lifetime. At both sides of each leg of the isosceles valve lamellae (24), a further thin triangular-shaped rigid lateral lamella (28R and 28L)—also called lateral blade—is attached in swiveling manner preferably by means of a film joint (plastic joint) (27), as illustrated here. The left lateral lamella of each main lamella is also connected to the right lateral lamella of the adjacent main lamella, again in swiveling manner preferably by means of a film joint. Each left lateral lamella represents a mirrored image of the right lateral lamella. This means, that between adjacent valve lamellae of a closed valve, one left and one right lateral lamella each are congruently placed over each other, radially oriented towards outside. In this position, the lateral lamellae (28R and 28L) reinforce the valve lamellae (24) against flection caused by blood pressure.

Furthermore they close the gap between the valve lamellae, thus ensuring excellent tightness of the valve. In order to enable the valve lamellae (24) always to close automatically, optionally springing elements (30) may be added in form of partial cylinders, preferably consisting of the same material. The blood backflow together with the blood pressure increases the closing speed and force as well as the tightness of the valve. The dimensions of the lateral lamellae determine the position of the valve lamellae in opened state, respectively the opening width of the valve. The attachment position of the joints to the edges of the hard blade, at the inner or the outer edge, determines whether the lateral blades during closure of the valves are guided to the front or to the rear side of the valve. This is essential for correct functioning of the valve.

The valve (17) is manufactured preferably by three-dimensional printing in one piece, consisting of plastics or a mixture of plastics and metal powder.

Figure 8:
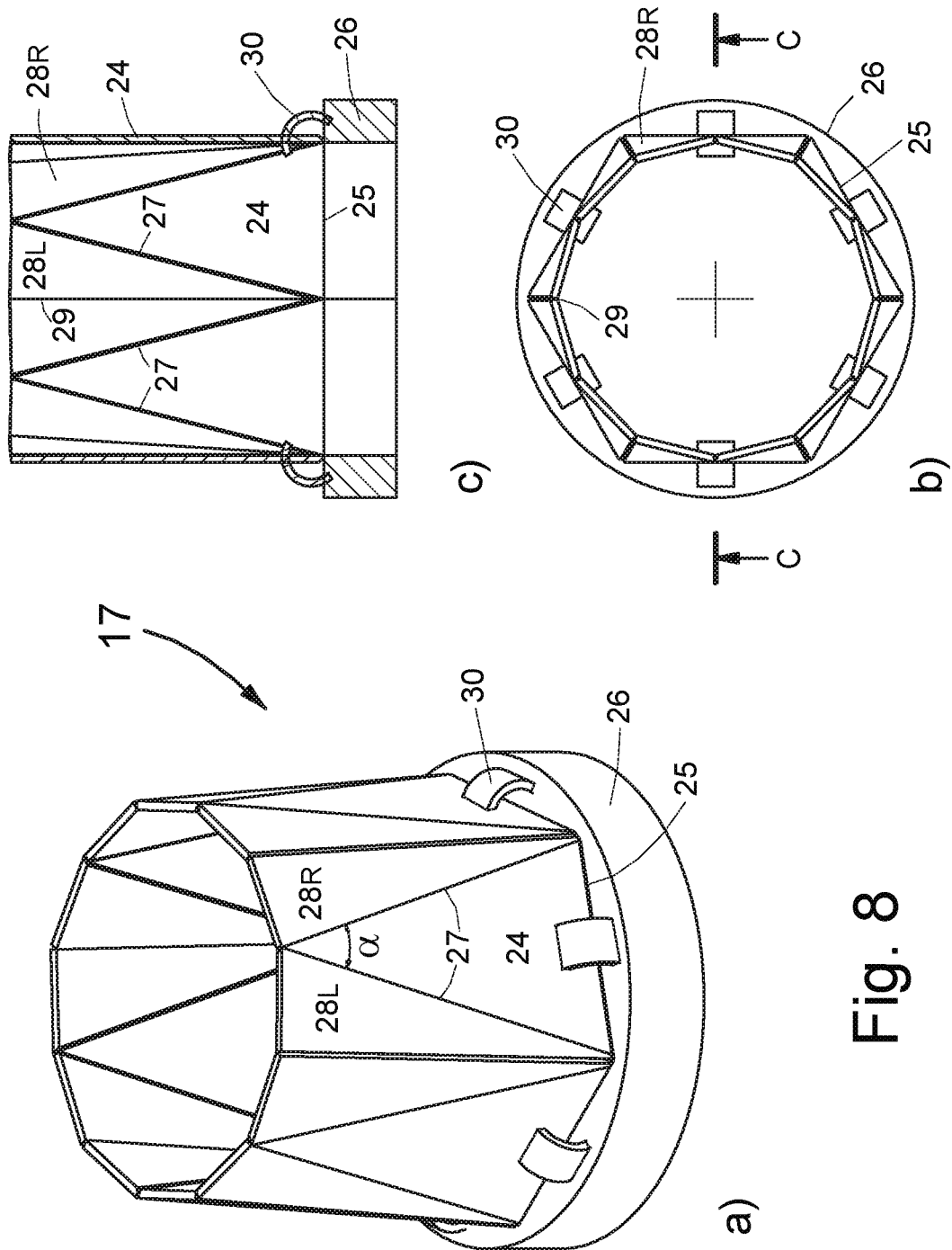
FIG. 8 the artificial check valve shown in FIG. 7 in opened state in three views (a, b and c). The six blades form together with the twelve lateral blades a foldable and lockable tube.

FIG. 8 shows three views (a, b and c) of the valve (17) in an opened state. This valve is composed of a valve ring (26) with hexagonal bore and six hard valve lamellae (24), attached in swiveling manner to the six edges of the hexagonal bore. By means of film joints (25), the valve lamellae are grouped in swiveling manner to the six edges of the hexagonal bore of the valve rings (26). Springing elements (30) between valve lamellae and valve ring enable the valve lamellae automatically to close in rest position, without blood flow.

Between two hard valve lamellae each, two triangularly shaped or triangular hard lateral lamellae (28R and 28L) are provided in mirrored configuration with respect to each other, with the tip pointing towards the valve ring (26). The lateral lamellae are mutually and with the main lamellae connected in a swiveling manner by joints, preferably by film joints (27 and 29).The lamellae feature different wall thicknesses, with the maximum thickness being located at the center of the lamella each, and decreasing towards the joints. As to the valve lamellae (24), the joints (25) are attached to the valve ring (26) at the inner edge, in order to enable them to be inclined from a nearly vertical position to the closing position by ca. 45° towards inside, i.e. to the center of the valve. The joints (27) at the two other faces of equal length of the valve lamellae are located at the edges oriented towards outside of the two valve and lateral lamellae. They move towards outside by ca. 45°. Between the two lateral lamellae (28R and 28L) mutually connected in mirrored configuration, the joints (29) are attached to the inner edges of the hard lateral lamellae, so that these lateral lamellae during closure of the valve automatically revolve towards the inside and finally are placed completely over each other. The wall thickness of the lateral lamellae is not uniform as well. The narrow outer edges, representing the outlet of the valve, are thicker than the tips which are closer to the valve ring (26).

The joints at the lateral lamellae are preferably modeled only partially, like a half of a piano hinge, preventing or at least reducing material accumulation at the corners, where several valve lamellae, with or without lateral lamellae, come into contact.

For valve lamellae and lateral lamellae, the faces featuring a film joint, dispose of a clearly visible thickness easy to measure with two edges clearly to identify each. Whereas one edge is provided in the form of a film joint springing back, the other one acts as angle limitation of the swivel. This mechanism has been conveniently configured so that the valve disposes of defined and safe mobility and motion cycle and a stable run.

Figure 9:
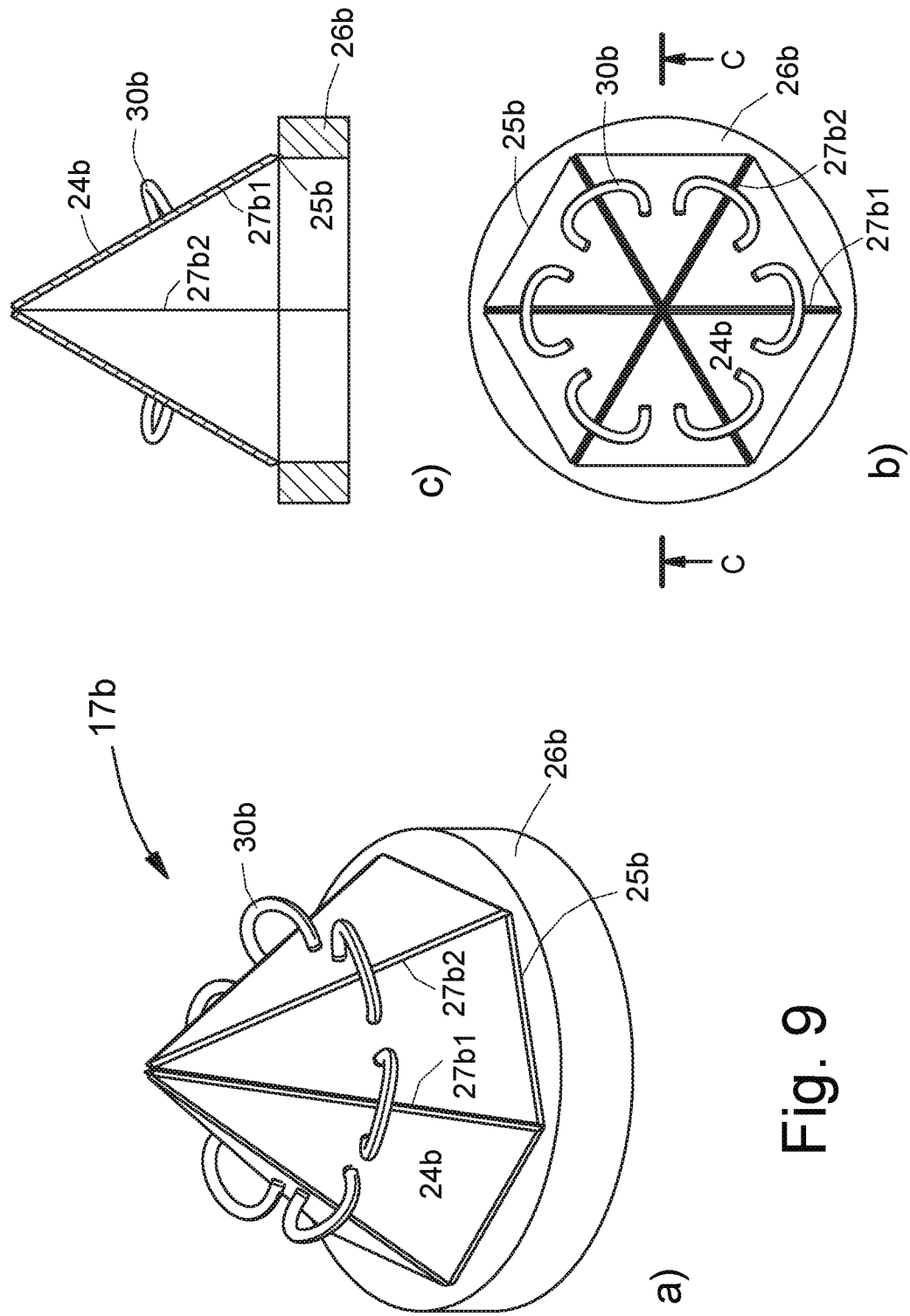
FIG. 9 a simple artificial check valve in closed state, with possible use as heart valve, in three views (a, b and c).

FIG. 9 shows a simple version of the closed valve (17*b*) in three views (a, b and c). This valve is composed of only three parts (24*b*, 26*b* and 30*b*). By means of film joints (25*b*), the hard valve lamellae (24*b*) are attached to the valve ring (26*b*) in swiveling configuration. The semicircular springing elements (30*b*) for this valve are accommodated between two adjacent valve lamellae. The entire valve (17*b*) is manufactured in one piece by three-dimensional printing, consisting of plastics or a mixture of plastics and metal powder.

Figure 10:
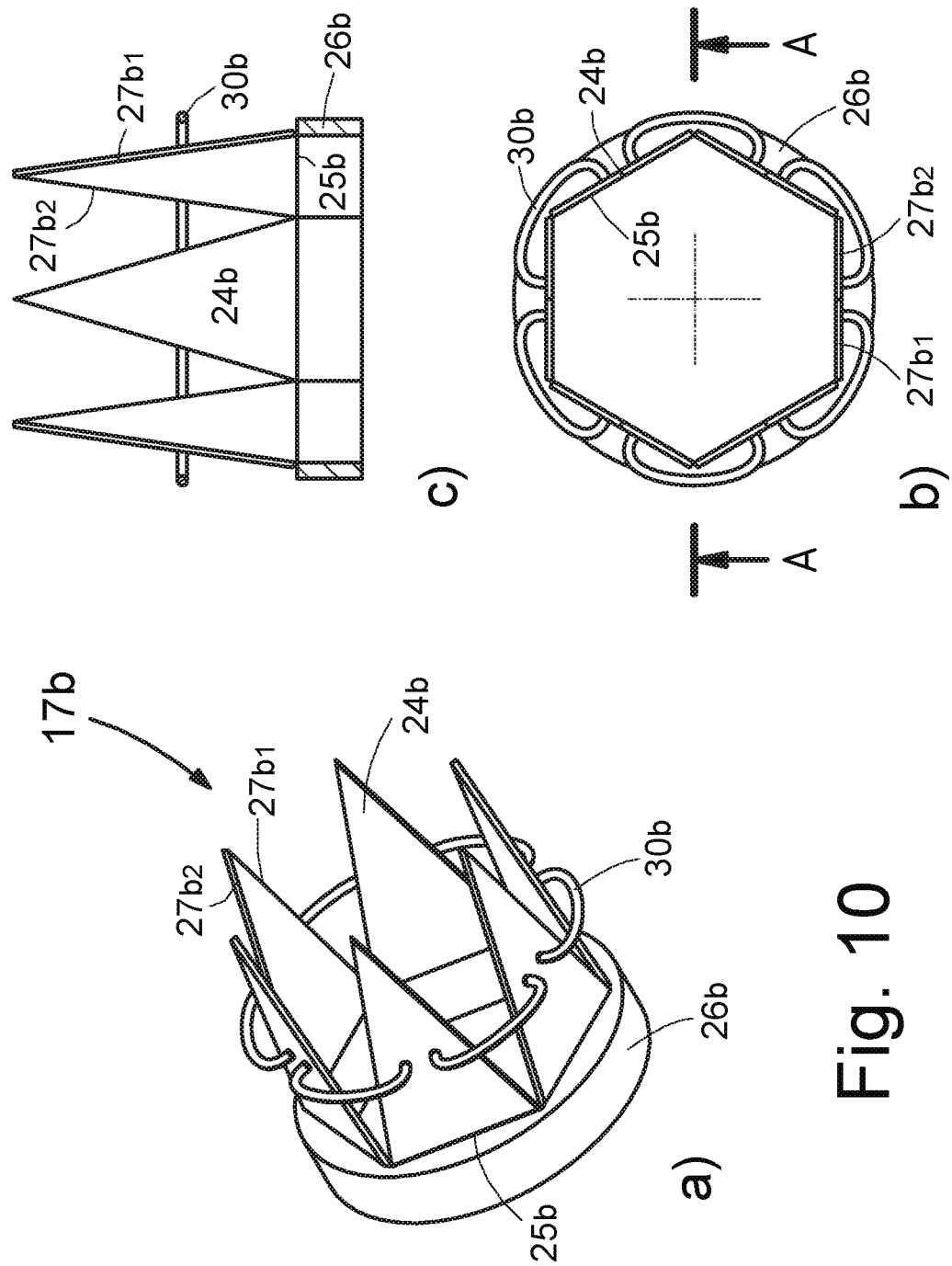
FIG. 10 the simple artificial check valve illustrated in FIG. 9 in opened state in three views (a, b and c).

FIG. 10 shows three views (a, b and c) of the valve (17*b*) in opened state. The sides of equal length (27*b*1 and 27*b*2) of the hard valve lamellae (24*b*) are at the left and at the right side positively and negatively formed (convex and concave), so that they always slide into each other during and after closing. This prevents spilling over or breaking through of individual valve lamellae, thus ensuring tightness of the configuration.

Figure 11:
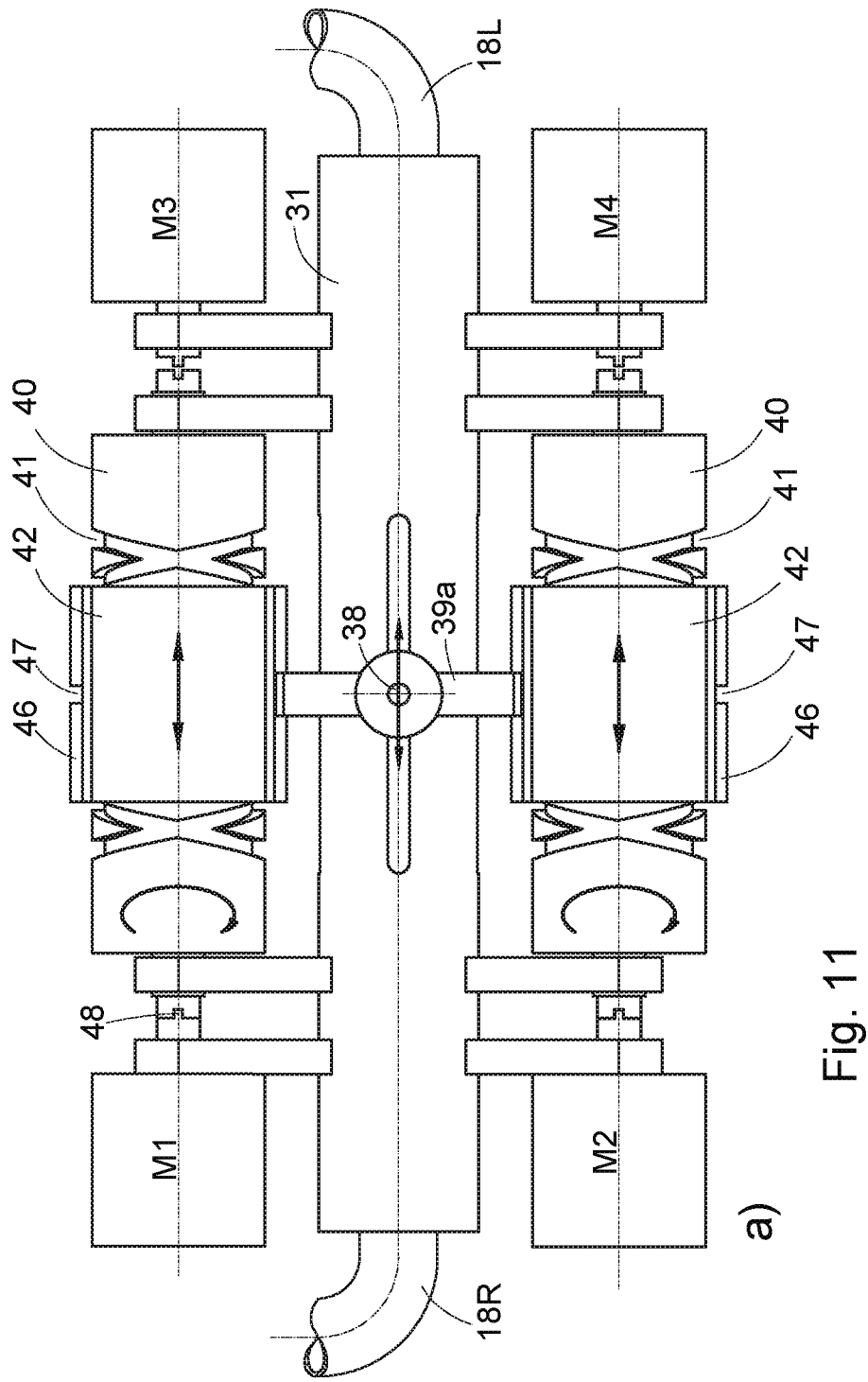
FIG. 11 an electro-hydraulic pump unit with a double-piston cylinder unit in tandem configuration and two spindle drives placed at both sides of the cylinder as redundant drive, actuated by electric motor, in three views (a, b and c). View (a) represents a top view, (b) a side view and (c) a longitudinal section of the three mutually connected units.
Figure 11:
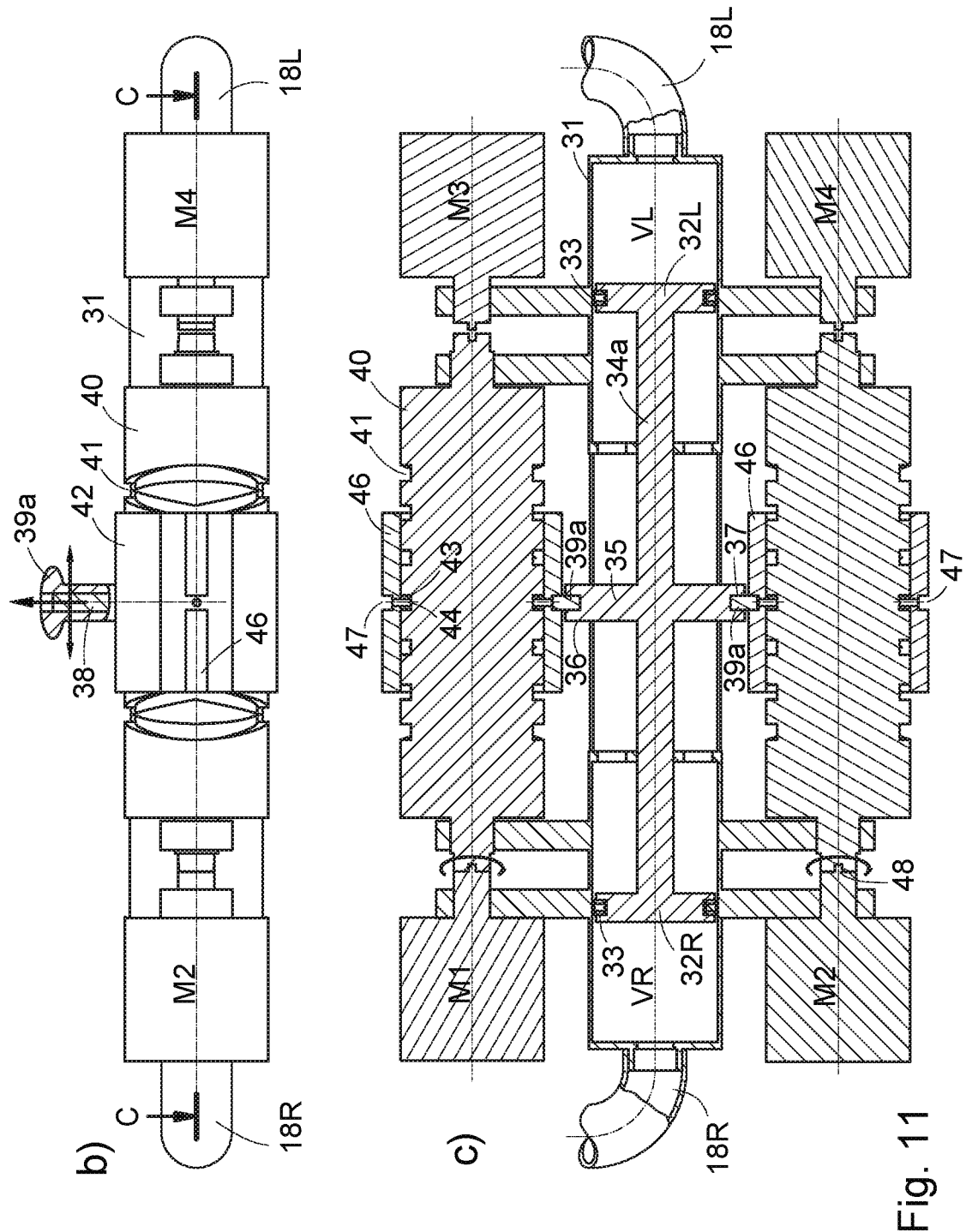

FIG. 11 shows a pump unit in three views, top view (a), lateral view (b) and longitudinal cut (c), with a cylinder-double piston unit (31, 32L and 32R) in tandem configuration as pump, and two spindle drives (40 and 42) for transmission, actuated by two to four electric motors (M1, M2, M3 and M4), grouped at both sides of the pump. The pump is equipped with a cylindrical case (31) accommodating the cylinder bore with double piston (32R and 32L), piston seals (33) and the common piston rod (34*a*). In front of each working space (VR and VL), the pump at each side features a connector for drive fluid. Through those connectors, the drive fluid flows in an alternating sequence in turn through the lines (18R and 18L) into the drive chambers of the two halves of the heart, squeezing the blood from the blood chambers into the pulmonary arteries respectively into the aorta. If it is intended to make the blood chambers of each half of the heart squeeze the blood simultaneously or cyclically into arteries respectively and aorta, the two pumps in simple version (i.e. with one piston each) have to be placed in parallel at both sides of the motor-gearing unit, and the piston rods are attached to the gearing of the drive unit by means of a manually switchable coupling.

Within the cylinder space, the piston rod (34*a*) includes of two bearings. Between these bearings, a ring-shaped element (35) is inserted, which acts as drive of the piston rod (34*a*). At both sides of this item (35), coupling elements (36) are provided protruding from both sides of the pump case through two oblong holes, used for actuation by gearings driven by electric motor, like spindle drives, worm drives, crank drives, eccentric drives, slider-crank mechanisms, rope, belt and chain drives or other known drive mechanisms. Furthermore the ring-shaped element (35) features a pin (38) as an arm, rising vertically towards outside, protruding between the two coupling elements (36) perpendicularly to the piston rod from the pump case though an oblong hole. The arm (38) is used as fixture and guide of a manual coupling (39), and in common with it also as manual actuation of the piston rod (34*a*) after failure of the electric drive.

The coupling (39) features a handle with a round button at its end. When pushing up and down the handle, the connection between the piston rod (34*a*) and driven element (42) of the gearing is separated or reengaged, by shifting the tip of the coupling (39) out from the recesses (37 and 47) of the coupling elements (36 and 46), or reinserting it at this position. As soon as the coupling (39) has been disengaged, the artificial heart can be operated further by manually acting on handle and arm (38 and 39) towards the right and towards the left.

In a simple configuration, the pump is actuated by one or two electric motors (M1 or M2) and a gearing which transmits the rotary movement of the electric motor into a translational movement back and forth. The driven element (42) of the gearing moving in a translational manner features a coupling element (46) with a recess (47) like the recess of the driving element (37) of the piston rod.

Figure 12:
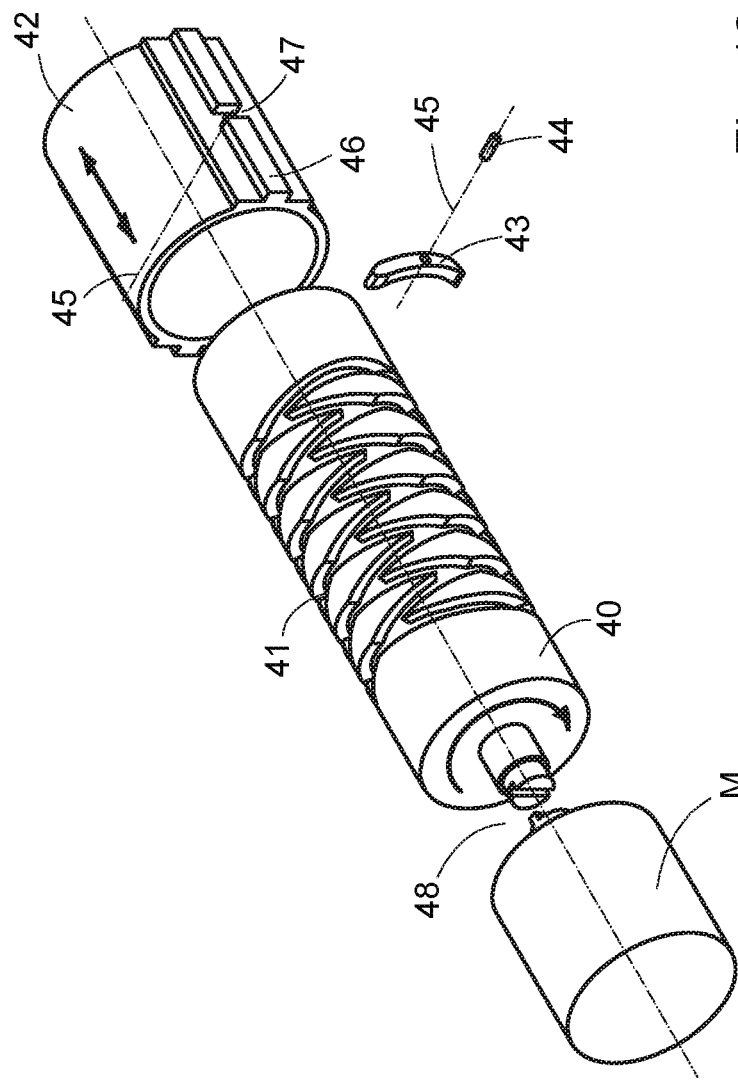
FIG. 12 a motor-gearing unit as drive for the pump of the drive chambers. An electric motor continuously rotates a drum in one direction, which acts as spindle. A spindle nut in form of a sleeve with two internal sliding bodies moves back and forth on the drum, driving the piston rod of the pumps by means of a manually actuated coupling.

FIG. 12 shows a preferred drive option of the pump, composed of an electric motor (M), driving a cylindrical body (40) by means of a coupling with one way clutch (48) like a drum with grooves, as a spindle at constant angular speed in one direction. The cylindrical surface of the drum features two grooves (41) in opposite direction, running at the right and at the left spirally-shaped and tangentially inside each other, in double-start configuration. Each groove spiral at the right and at the left forms an infinite self-contained loop. The two infinite loops are grouped on the surface of the spindle, rotated by 180° with respect to the rotary axis of the drum. Above the drum, in coaxial orientation a sleeve (42) is provided, as a part of the spindle nut. The sleeve at both sides features coupling elements (46) in form of projecting material, which may be dovetailed or feature recesses (47) or holes. The projecting coupling elements (46) are used on the one hand as anti-twist protection of the spindle nut, on the other hand to engage and disengage the electric drive of the cylinder-piston unit from the pump.

Furthermore the sleeve (42) features one or two mutually opposing radial holes with the hole axis (45), one or two bearing pins (44) mounted in rotatable manner within the bores, and one or two sliding bodies (43) respectively shuttles as sliding blocks, in which one of the bearing pins (44) each is firmly attached. The sliding body (43) is rounded from all sides to take place between three sides of the helical groove (41) and the sleeve (42) and rotate approximately ±15° around the axis (45) of the pin. Therefore it is also called shuttle. After assembly of the pump, rotation of the sleeve (42) is prevented by coupling (39). For this reason, the sleeve moves translationally along its longitudinal axis, until the sliding block (43) at the end of its groove spiral slides in a smooth manner hitchless and without jerk into the counter spiral, thus inverting the moving direction of the sleeve. For the double-start right and left spiral and 180° displacement of the grove passages, the two sliding bodies run as sliding blocks within the groove passages in mirrored orientation, symmetrically transmitting the force from the drum to the sleeve.

FIG. 13 shows the drum (40) rotating always in one direction with its double-start (1 and 2) helical grooves (41). The groove passages (1 and 2) each for itself form an infinite loop, one running at the right (1R and 2R) and one at the left (1L and 2L), merging at the beginning and at the end (E1 and E2) of their groove passages (1R and 1L) and (2R and 2L) smoothly, hitchless and without jerk together, meanwhile changing their moving direction. The right and left passages of each groove loop (1 and 2) are mirrored with respect to planes (F and G). The groove loops (1 and 2) are displaced by a rotary angle of 180°, so that with respect to plane (F) the passages (1R) with (2L) and (2R) with (1L) are in mirrored orientation.

Each groove loop (1 and 2) features a sliding body (43). Both sliding bodies are at each position of the spindle (40) opposite to each other in mirrored orientation, with respect to the rotary axis of the spindle. The spindle is equipped on both sides with bearing journals and coupling elements with one way clutch (48), ensuring a safe driving at one side or in a redundant manner at two sides.

Figure 14:
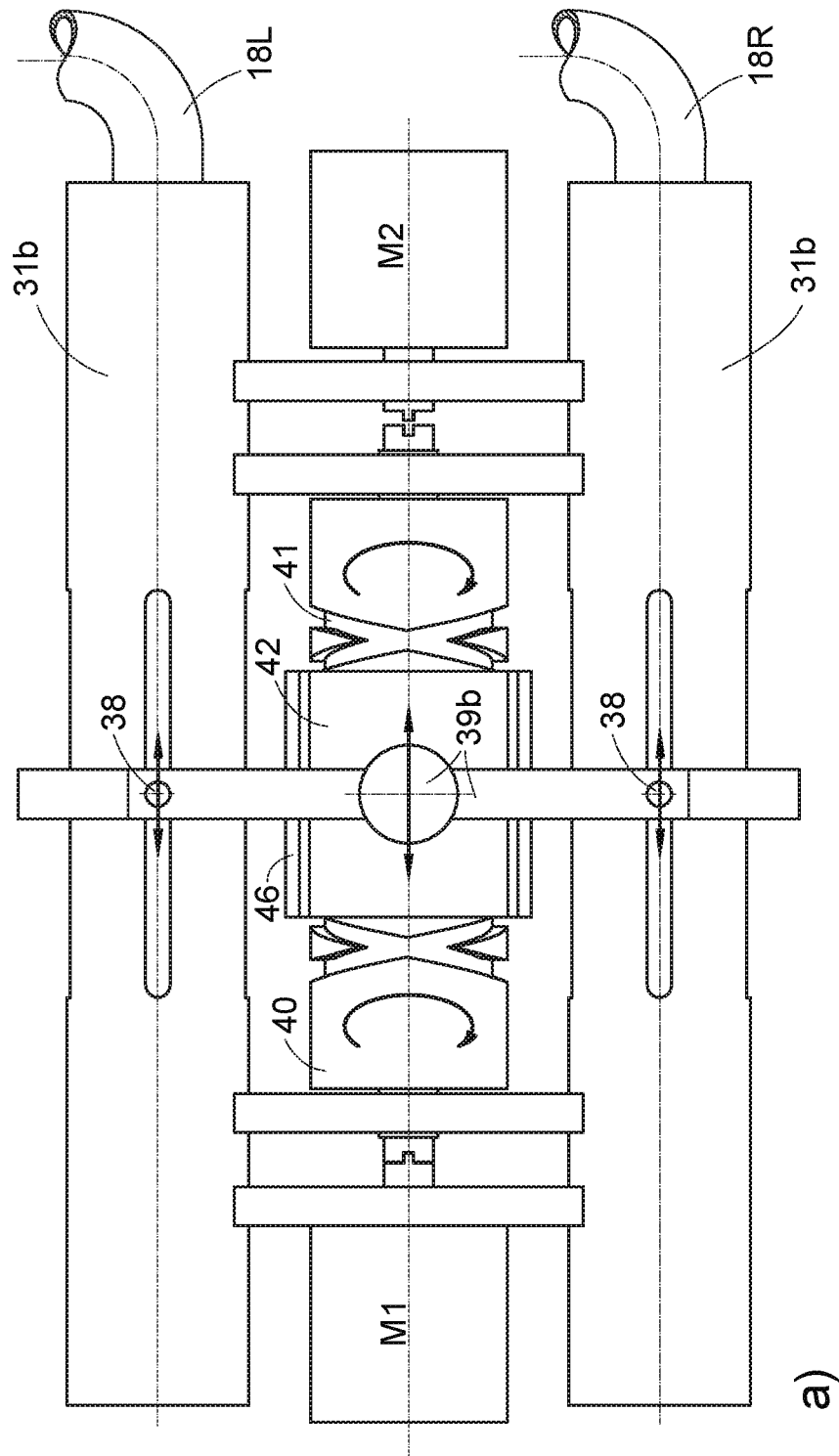
FIG. 14 an electro-hydraulic pump unit with two cylinder-piston units working cyclically in common mode and a spindle drive placed between the pumps, actuated by electric motor, used as drive, in three views (a, b and c). View (a) represents a top view, (b) a side view and (c) a longitudinal section of the three mutually connected units.
Figure 14:
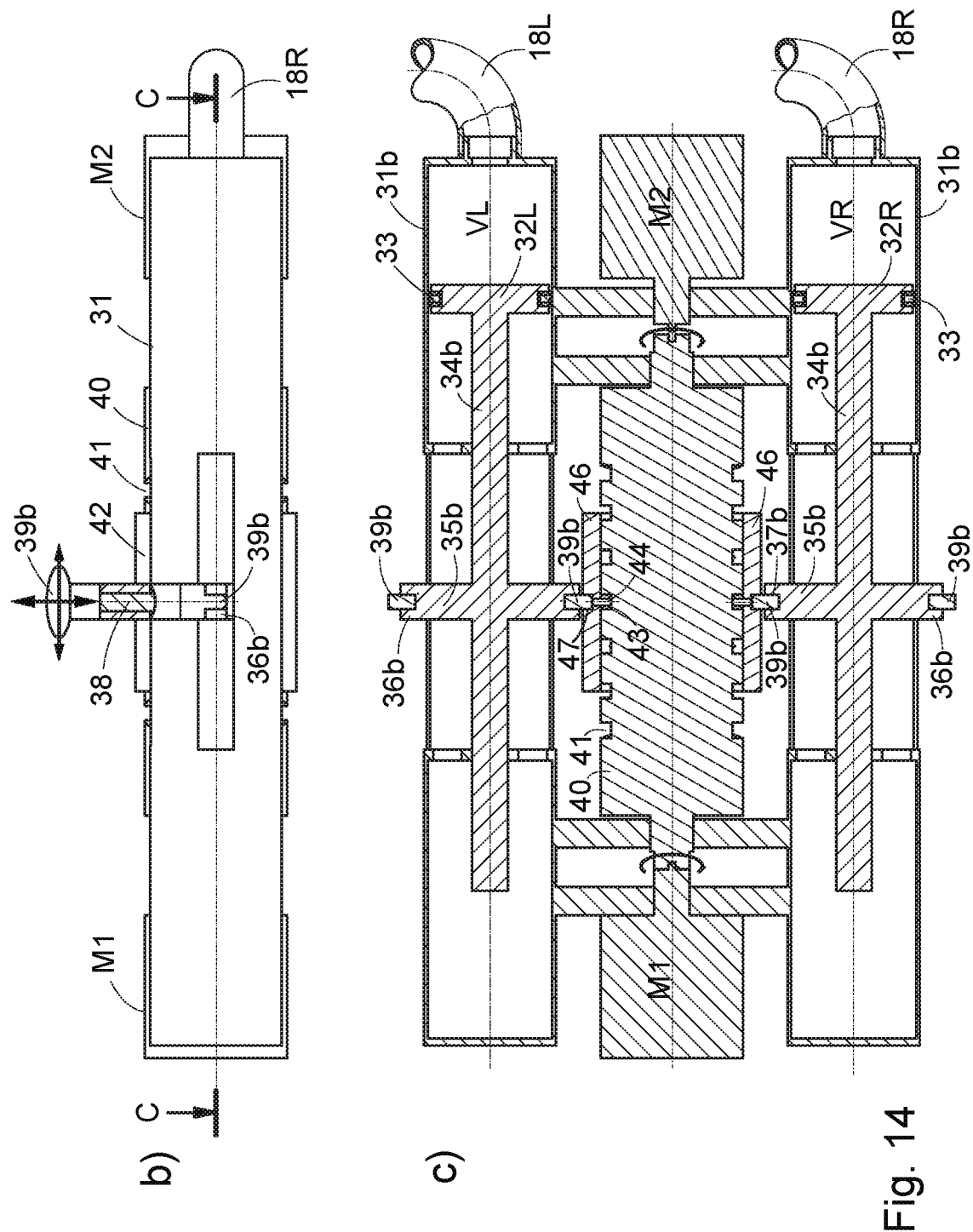

FIG. 14 shows a pump unit with two cylinder-piston units (31b, 32L and 32R) grouped individually and in parallel, in three views a, b and c.

The pump unit features a case (31b), with two cylinder holes located beside each other, accommodating the two pistons (32R and 32L) with their piston seals (33) and piston rods (34b). The pumps are actuated by one or two electric motors (M1 or M2) with a spindle drive (40 and 42) for transmission, located between the two cylinder-piston units, converting the rotatory movement of the motor into a translational movement back and forth of the piston rod (34b).

In front of their piston, each cylinder bore features a working space (VR and VL) with a connector for drive fluid. Through that connectors, the drive fluid flows through the lines (18R and 18L) in an identical cycle into the drive chambers of the two halves of the heart, squeezing the blood from the blood chambers into the arteries respectively into the aorta. The piston rods (34b) of the simple pump (31b) feature two bearings and a ring-shaped element (35b) each placed in between, acting as driving element. This driving element (35b) from both sides is equipped with coupling elements (36b), protruding from the pump case through oblong holes and used for actuation by gearings driven by electric motors, like spindle drives, worm drives, crank drives, eccentric drives, slider-crank mechanisms, rope, belt and chain drives or other known drive mechanisms. Furthermore, the ring-shaped elements (35b) feature at one side a round pin (38) each as arm, preferably protruding between the two coupling elements (36b) perpendicularly to the piston rod from the pump case though an oblong hole. The arms (38) are used as fixture and guide of a manual coupling (39b) and in common with it also as manual actuation of the piston rod (34b) after failure of the electric drive.

The coupling (39b) features a handle with a round button at its end, located centrally between the two pistons and above the spindle nut (42) of the gearing. When pushing up and down the handle (39b), the movement between the piston rod (34a) and coupling elements (46) of the gearing is separated or reengaged, by shifting the tip of the coupling (39b) out from the recesses (37b and 47) of the coupling elements (36b and 46) or inserting it at this position. As soon the coupling (39b) has been disengaged, the artificial heart can be operated further by the patient, by manually acting on handle and arm (38 and 39) towards the right and towards the left. This represents an improved cardiac massage and is safer than compressing the chest, which includes the risk of breaking the ribs.

For increased safety, each spindle (40) of the gearing is driven from both sides by two electric motors (M1 and M2), in the case of presence of one single gearing, or by (M1 and M3) and (M2 and M4) in the case of two bearings, rotating clockwise and counterclockwise. The couplings with one way clutch (48) between electric motors and spindle drives prevent sluggishness or blocking of the spindle rotation in the case of the failure of an electric motor.

Figure 15:
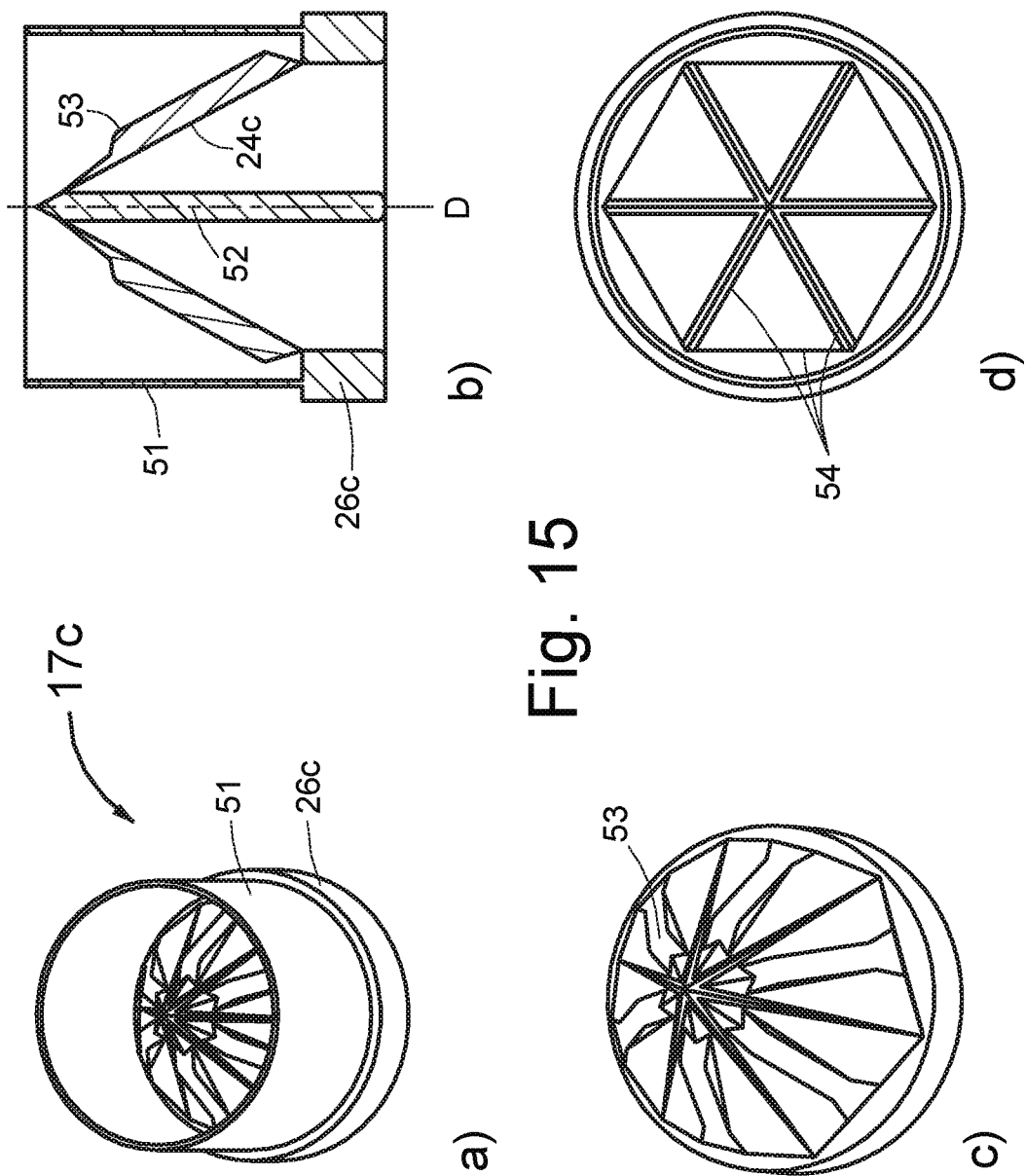
FIG. 15 in four views (a to d) a simple and safe version of the artificial check valve, used as heart and venous valve, and also in other industrial branches, e.g. in sewers.

FIG. 15 shows a safely working check valve (17c) easy to produce, used in medical technology as heart valve or venous valve, or in other branches like waste water technology or chemical industry.

A valve ring (26c) is provided in a tube-shaped hollow case (51), acting as a step with a through hole respectively bore, at least triangularly- or preferably hexagonally-shaped. Each face of this hole forms a hollow geometrical body with four triangular faces like an asymmetric pyramid, with one of these faces forming an isosceles triangle, as shown in top view d). Two faces are identical and feature a common edge (52) on the center axis (D) of the case. The other two faces are consistently hollow, enabling a gaseous or liquid medium to flow through along the axis (D). Multiple grouping of the hollow body formed this way, according to the number of faces of the polygonal bore, around the axis (D) generates a pyramidal grid (54) within the tube piece (51), open from both sides for gases and liquids. A very stable check valve for one flow direction can be constructed by attaching in a swiveling manner triangular-shaped valve lamellae to the sides of the polygonal hole over the grid structure. The rear side of the valve lamellae features bulge-shaped ribs (53). They are used on the one hand to reinforce the valve lamellae against sagging, on the other hand for limitation of the valve opening, by being placed directly contacting the walls of the case (51).

FIG. 16 shows under a) a cross section through the mechanical coupling (39a) between the two drive systems (40 and 42) and the cylinder-piston unit (31 and 32) According to FIG. 11 perpendicularly to the piston rod (34a), and under b) a cross section through the mechanical coupling (39b) between the drive system (40 and 42) and the two cylinder-piston units (32 and 34b) According to FIG. 14 perpendicularly to the piston rod.

FIG. 17 shows a quick connection of veins and arteries with connectors (4, 5 and 6) of the half shells of the heart. For the connectors, positive bulges (55) are provided, According to view a). After pulling a sleeve (15, 16 or 49) of one of the bags (12 or 13) over its connector, and putting over it a vein, artery or hose, the quick connection (56) is placed all around, held in place by the barbs (58a and 58b) and locked by the slide gate (59). The quick connection features, as shown in lateral view c), negatively formed indentations (60) matching the bulges (55) of the connectors. The slide gate (59) features a two-part safety nose (71a and 71b) preventing opening by mistake.

FIG. 18 shows a seamless blood bag (12) consisting of synthetic or biological fabric or textile, featuring preferably a three-dimensional ellipsoid shape. Its size corresponds to a complete half of the heart. Inlet and outlet (15 and 16) are provided, preferably cylindrically woven together with the blood bag in one single piece.

In its upper half (12.1), the structure of the blood bag together with the connections is relatively thin. After insertion into the upper hard half shell, this zone (12.1) remains nearly immobile in its position at the wall of the upper hard half shell. The lower half (12.2) is thickened like a sickle or a parabola, with maximum thickness in the lowest point, parabolically decreasing all around towards the center plain of the bag (E). Thickening process usually takes place by applying a highly elastic material like polycarbonate urethane (PCU) by means of a 3D printer on the rear side of the blood bag, so contact to blood is avoided.

FIG. 19 shows a seamless drive bag (13), consisting of synthetic or biological fabric or textile as well. The weaving process for this bag together with its connection (49) is carried out in one piece as well, the shape is three-dimensionally ellipsoid, the size corresponds to the complete half of a heart, and a preferably cylindrical connection (49) used as in- and outlet is provided.

Within the zone of the lower half (13.1)—i.e. below the center plane (E)—, the woven structure of the drive bag is thin; this zone remains in nearly immobile state at the wall of the lower hard half shell. The upper half (13.2) is thickened like a sickle or parabola. The thickening feature starts all around from the level of the center plane (E), reaching its maximum value in the upper point. The parabolic thickening of the mobile half of at least one of the two bags ensures that the bending wave (63), respectively deformation wave, of the bags explicitly starts from the center, i.e. from plane (E), reproduced all around along the wall of the hard half shells up to the upper respectively lower cardiac apex.

The drive bag designed this way migrates independently of its position and direction of motion, so that the end or tip of the bag is always the last section to be inverted, as thickness as well as resistance to bending in this position is maximum.

When plugging together two half shells of the half of a heart, the lower half of the blood bag (12.2.) is placed loosely onto the upper half (13.2) of the drive bag. These two bag halves are placed on top on each other preferably with a gel-like substance like paraffin in between, migrating respectively swimming between the two liquids in question, blood on the one side and drive fluid on the other side, stress less without formation of wrinkles and kinks, back and forth or up and down, depending on the position of the body. As the bags are located on top of each other, normally only one of them has to be parabolically thickened.

FIG. 20 shows a blood bag with the lower half (12.2) being annularly elliptically toothed. The shape of the teeth (61) is preferably circular, but other shapes like an involute, a cycloid or other designs usual for gear tooth forming are also possible. The thickening increases with increasing distance of the rings to the center plane (E).

FIG. 21 shows a drive bag with the upper half (13.2) being toothed annularly elliptically all around. Dovetailing of the drive bag (62) with respect to dovetailing of the blood bag is displaced by one tooth each. When both bags are placed on top of each other, a tooth of the one bag is always inserted into a tooth gap of the other bag.

FIG. 21c shows the profile of an elliptic annular gear (62) of the drive bag (13) in two positions (62a and 62e). Profile (62a) visualizes the state of the annular gear, when the drive bag is completely empty and its upper half (13.2) is located inside the lower half (13.1) (see 13a in FIGS. 28 and 29). Profile (62e) on the other hand shows the state of the annular gear, when the drive bag is completely filled, as illustrated in FIG. 21b) (see 13e in FIGS. 28 and 29). The material of the two bags cannot be stretched, whereas the material of the dovetailing is elastic. When rotating the annular gears around their elliptical center axis of their profile, their resistance to twisting in different positions is not identical. For this reason, they remain in their position during the movement of the bags from the one half to the other half of the hard shell, as long as they are floating between the liquids, until they reach the wall of the opposite hard shell. As soon as the outermost point of each annular gear reaches the hard shell, the drive medium pushes or pulls the zone located inside the annular gear, and causes rotation of the annular gear from one stable position to a second stable position. The thickest annular gears are the last elements to be inverted during each movement, as they dispose of maximum resistance to torsion.

A combination of thickening and/or dovetailing of blood and/or drive bag is possible anytime.

FIG. 22 shows an entire artificial heart, composed of two halves (1R and 1L). Each half of the heart features a hard shell, composed of two half shells (2 and 3) plugged together and hermetically tighten. Each half shell accommodates a bag (12 and 13). The volume of this bag corresponds to the volume of the entire half of the heart. The upper half of the blood bag (12) is located in the upper half shell, nearly immobile. Its lower half is parabolically thickened and free moveable.

One half of the drive bag (13) is located in the lower half shell, nearly immobile. In this illustration, it is not thickened.

One half of these bags is relatively immobile, located on the inside of the half hard shell, whereas the second halves are placed back to back, migrating together, as illustrated here, from position a (in which both blood bags are full) traversing b, c and d up to e (in this position both halves of the heart are completely empty). Both halves of the heart work synchronously like a natural heart. This phase corresponds to the systole.

FIG. 23 shows the synchronous motion of the two mobile halves of the two bags in the artificial heart illustrated in FIG. 22, in the diastolic phase from position e (=empty), traversing positions f, g and h to position a (=full). The different wall thickness of one of the two bags ensures that both bags, when migrating along the wall of the hard shell from center plain (E) in one or the other direction, are bended up, this way completely and laminarly emptying the blood bag.

FIG. 24 shows an entire artificial heart composed of two halves (1R and 1L) with one toothed blood bag (12) and one toothed drive bag (13) each, in the systolic phase. Both halves of the heart work synchronously. With respect to the movement of the halves of the bags, the effect of the dovetailing of the rear sides of the two bags is identical to the effect of the thickening of the halves. Dovetailing of the bags corresponds to a partial or irregular thickening. For this reason, the outer envelope of a thickened bag can also be modeled in an undulated manner. This measure corresponds to a combination of thickening and dovetailing.

FIG. 25 shows the artificial heart illustrated in FIG. 24, this time during the diastolic phase. Both halves of the heart aspirate the blood from the periphery of the body and from the lungs.

FIG. 26 shows an artificial heart beating asynchronously with a thickened blood bag (12) according to this invention. Whereas the right half of the heart aspirates the blood from the body, the left half presses it into the aorta.

FIG. 27 shows the asynchronously beating artificial heart illustrated in FIG. 26, now in the opposite phase. Whereas the right half of the heart pumps the blood into the pulmonary artery, the left half simultaneously aspirates the oxygen-rich blood from the lungs. Theoretically the quantity of blood pumped through the lungs during each heartbeat by means of a heart asynchronously beating this way, exceeds the quantity delivered by a natural heart, since the latter one during the relaxation phase is not able to aspirate the blood like a forcibly guided pump. An artificial heart pulsating this way causes even negative pulsation of larger veins due to the suction effect.

FIG. 28 shows an asynchronously beating heart pulsating according to FIG. 26, but with dovetailed blood and drive bags.

FIG. 29 shows an asynchronously beating heart pulsating according to FIG. 27, but with dovetailed blood and drive bags.

FIG. 30 shows a double-piston pump unit composed of a two-piece case (31cL and 31cR), a piston rod (34c) with a piston on both sides (32bR and 32bL) without sealing. Centrally between the two pistons, the piston rod (34c) features the drive element (or the ring shaped element) (35) with the coupling element (36) and the recess (37). Two separate working chambers (VR1 and VL1 and VR2 and VL2) are provided in front of and behind the two pistons each. The working chambers at the right (VR1 and VR2) and at the left (VL1 and VL2) are connected by a hose each (18R and 18L), mutually and to one of the drive bags. Two relief valves are provided for each piston, consisting of a through bore (64), a retaining ball (65), a pressure spring (66) and a cannulated adjusting screw (67). The volume of each working chamber is larger than the volume of the necessary drive medium such that the overrun flows from one piston side to the other piston side through the relief valves and over the pistons by each stroke.

A pump designed this way manages without piston seal, as the drive fluid flowing from one side to the other side of the piston, passing along the piston or through the relief valve, returns along the same path when the piston moves in opposite direction. This configuration represents a self-contained hydraulic system increasing extra the safety and the working life of an artificial heart, decreasing the piston friction and the energy consumption.

The features detailed in this description, in drawings and claims, may be relevant for the realization of the invention, individually as well as in any combination.

REFERENCE DESIGNATIONS

1: Half of the heart
2: Upper half shell
3: Lower half shell
4: Blood inlet opening
5: Blood outlet opening
6: In- and outlet for drive medium
7: In- and outlet for lubricating agent
8: Lower edge of upper half shell
9: Edge of lower half shell
10: Sealing ring, O-Ring
11a: Positive fastener of half shells
11b: Negative fastener of half shells
12: Blood chamber and/or blood bag
13: Drive chamber and/or drive bag
14: Gap between blood and drive bags
15: Sleeve=Inlet of blood bag
16: Sleeve=Outlet of blood bag
17: Artificial valves (three versions a, b and c)
18: Line respectively hose of drive medium
19: Line respectively hose of lubricating agent
20: Bore respectively connector of lubricating agent
21: Bore for accommodation of miniature camera
22: Bore for accommodation of pressure sensor
23: Ring gap at the equator of the two half shells 23a: Longitudinal grooves within the half shells
23b: Ring-respectively transversal grooves within the half shells
24: Hard respectively rigid valve lamella (three versions -, b and c)
25: Swivel joint (film joint) between valve lamella nd valve ring
26: Valve ring (three versions -, b and c)
27: Swivel joint (film joint) between valve lamella and lateral lamella
28: Lateral lamella
29: Swivel joint (film joint) between two adjacent lateral lamellae
30: Bow-shaped springing elements, elastic shackle
31: Case of cylinder-piston unit
32: Piston of cylinder-piston unit
33: Piston seal
34: Piston rod (two versions a and b)
35: Round disc as driving element of piston rod
36: Coupling part respectively coupling element of piston rod
37: Recess within coupling element 36
38: Pin as arm or lever
39: Manual coupling with handle or knob
40: Spindle, spindle drum
41: Helical grooves on spindle drum
42: Sleeve as spindle nut
43: Shuttle as sliding block
44: Bearing pin
45: Axis of radial bore in sleeve wall
46: Projecting part of spindle nut (sleeve) as coupling element
47: Recess in 46
48: Coupling with one way clutch
49: Sleeve=Connection of drive bag
50: Convex lenticular pad filled with viscous material
51: Ring-shaped hollow case, tube piece
52: Common edge of hollow and triangular-shaped asymmetric pyramids
53: Bulges as reinforcement ribs and limitation of opening of valve lamellae 24c
54: Pyramidal grid structure
55: Bulge of connectors of the halves of the heart
56: Vein or artery
57: Arched plastic tape as quick release
58: Barb
59: Slide gate with safety nose
60: Negatively arched surface=Indentations
61: Tensile strength material and ring-shaped thickened respectively dovetailed parallels of latitudes of blood bag
62: Tensile strength material (thread) and ring-shaped thickened respectively dovetailed parallels of latitudes of drive bag
63: Bending wave, respectively deformation wave
64: bores of the piston
65: Valve ball of pressure limiting valve (relief valve)
66: Spring of relief valve
67: screw of relief valve
71: Safety nose
A: Longitudinal axis of the half of the heart
B: Bending axis of the elastic connection between the two halves of the heart
C: Central plane between the two halves of the heart
D: Axis of valve case E: Plane perpendicularly to the longitudinal axis (A) through the equator of the half of the heart
F: Plane through the drum
G: Plane through the drum perpendicularly to F
H: Plane along the center of the artificial heart perpendicularly to plane C
V: Volume of the entire half of the heart=maximum cardiac output
n: Number of faces of the valve ring=Number of valve lamellae (main blades of the heart valves)

The invention claimed is:

1. A half of an artificial heart, comprising a hermetically sealed hard shell as a housing of said half of said artificial heart, said half of said artificial heart having a blood chamber including an inlet and an outlet and a drive chamber including a connection as an in- and outlet, comprising:
    said hard shell being divided into at least a first half shell and a second half shell;
    wherein said first half shell includes an inlet and an outlet opening;
    wherein said second half shell includes an opening and a means to accept a drive medium;
    wherein a first portion of said blood chamber up to a first half of said blood chamber is attached to at least a portion of said first half shell;
    wherein a first portion of said drive chamber up to a first half of said drive chamber is attached to at least a portion of said second half shell;
    wherein a second portion up to a second half of said drive chamber is in contact with a second portion up to a second half of said blood chamber;
    wherein when said portion of said second half of the drive chamber moves, the contact between said drive chamber with said blood chamber produces a circumferential bending wave along the second portion of the blood chamber; and
    wherein said second portion of said blood chamber moves into a hollow portion of said first half shell and into a hollow portion of said second half shell alternately, with reduced stress and stretching.

2. The half of the artificial heart of claim 1, wherein portions of at least one of said blood chamber and said drive chamber is woven from a biologic thread.

3. The half of the artificial heart of claim 1, further including an elastic pad located between said second portion of said blood chamber and said second portion of said drive chamber.

4. The half of the artificial heart of claim 3, wherein said elastic pad is a lenticular convex-shaped elastic pad.

5. The half of the artificial heart of claim 1, wherein at least one of the second portion of said blood chamber and the second portion of said drive chamber is circumferential three-dimensional like a parabolic arc thickened.

6. The half of the artificial heart of claim 1, wherein circumferential latitude shaped teeth are present on the rear face of the second portion of said blood chamber and circumferential latitude shaped teeth are present on the rear face of the second portion of the said drive chamber.

7. The half of the artificial heart of claim 6, wherein the gear teeth are one of bulges generated by material accumulation, by insertion and incorporation of rigid rings, particularly mutually inserted like chain links.

8. The half of the artificial heart of claim 1, wherein said drive medium is a liquid.

9. The half of the artificial heart of claim 1, wherein a geometrical shape of said hard shell is in the shape of a two or three-dimensional ellipsoid.

10. The half of the artificial heart of claim 1, wherein said first half shell and said second half shell are connected together by means of a positive and negative interlocking connection with a circumferential cone shaped interface.

11. The half of the artificial heart of claim 1, wherein said hard shell further includes longitudinal and transversal grooves at an inner surface of said hard shell.

12. The half of the artificial heart of claim 1, wherein said hard shell further included a third chamber between the blood chamber and the drive chamber with an external connection for accommodation of a viscous lubricating and sealing agent.

13. The half of the artificial heart of claim 12, wherein said third chamber contains a means for regulating of cardiac output.

14. The half of the artificial heart of claim 1, wherein said hard shell includes one positive and one negative cylindrical connecting elements at close quarters on one side and designed such that by turning said hard shell 180° with respect to its longitudinal axis (C), said hard shell can be connected to a second hard shell which contains a second half of an artificial heart wherein the combination of the hard shell including said half of the artificial heart with the second hard shell which contains said second half of the artificial heart a complete artificial heart is formed.

15. The half of the artificial heart of claim 1, the circumferential bending wave produced is along the inside surface of the hard shell.

16. The half of the artificial heart of claim 1, where the stress, stretching and folding associated with the movement of said second portion of said blood chamber moving into a hollow portion of said first half shell and into a hollow portion of said second half shell is eliminated.

17. The half of the artificial heart of claim 1, further including an electro-hydraulic pump unit comprising:
    a cylinder-double piston unit including two pistons, a common piston rod located between said two pistons, and at least one working space per piston (VR & VL) wherein said cylinder-double piston unit, two pistons, common piston rod and at least one working space per piston is located within a cylindrical case;
    further including a driving element of said common piston rod attached to said piston rod and at least one coupling element wherein one portion of said coupling element is attached to said driving element and a second portion of said coupling element extends outside said cylindrical case;
    at least one drive mechanism positioned outside said cylindrical case, said drive mechanism connected to said driving element by way of the portion of the coupling element that extends outside said cylindrical case and
    wherein said cylinder-double piston unit includes connectors for drive fluid.

18. The half of the artificial heart of claim 17, wherein each of said at least one drive mechanism of said electro-hydraulic pump unit is actuated by at least one electric motor positioned at least at one end of said drive mechanism;
    further including a one-way clutch attached to each of said at least one electric motor;
    further including a cylindrical body attached to said one-way clutch wherein a surface of said cylindrical body includes two grooves in opposite direction, running at right and at left spirally-shaped and tangentially inside each other in a double-start configuration; and wherein said cylindrical body drives a means and wherein the means drives said common piston rod and wherein said driving element is a ring shaped driving element.

19. The half of the artificial heart of claim 17, further including:
a manually actuated coupling element to engage and disengage said driving elements from said driving element of said common piston rod to permit drive medium to be manually propelled into said artificial heart.

20. The half of the artificial heart of claim 17, wherein said a gearing of said drive mechanism is actuated by one of a spindle drive, worm drive, crank drive, eccentric drive, slider-crank mechanisms, rope, belt, and change drives or other known drive mechanisms.

21. The half of the artificial heart of claim 17, further including two separate working chambers in front and behind each of said pistons.

22. The half of the artificial heart of claim 21, further including a hose wherein said house is connecting said working space for the first of said two pistons and said working space for the second of said two pistons.

23. The half of the artificial heart of claim 21, further including at least one relief valve for each of said two pistons.

24. The half of the artificial heart of claim 23, wherein each of said relief valves includes a through bore, a retaining ball, a pressure spring and a cannulated adjusting screw.

25. The half of the artificial heart of claim 21, wherein the volume of said working space for each of said two pistons is larger than the volume of said hard shell.

26. The half of the artificial heart of claim 25, wherein drive medium is transferred from one piston side to the other piston side through said relief valves.

27. The half of the artificial heart of claim 25, wherein drive medium is transferred over each of said pistons.

28. The half of the artificial heart of claim 17, wherein said electro-hydraulic pump unit includes a spindle drive consisting a spindle screw and a spindle nut, wherein
the spindle screw comprised a (double) right-left infinite loop in the shape of a helical groove and
the spindle nut consists of a hollow cylinder without thread like a tube piece, within at least one sliding block is provided in form of a three-dimensionally curved and rounded shuttle, which slides hitshlessly and without jerk in the groove of said spindle screw.

* * * * *